US012717961B2

(12) United States Patent
Lamp

(10) Patent No.: US 12,717,961 B2
(45) Date of Patent: Aug. 25, 2026

(54) PRIVATE SYNTHETIC TIME SERIES DATA GENERATION

(71) Applicant: Dexcom, Inc., San Diego, CA (US)

(72) Inventor: Josephine Lamp, Charlottesville, VA (US)

(73) Assignee: Dexcom, Inc., San Diego, CA (US)

( * ) Notice: Subject to any disclaimer, the term of this patent is extended or adjusted under 35 U.S.C. 154(b) by 236 days.

(21) Appl. No.: 18/475,847

(22) Filed: Sep. 27, 2023

(65) Prior Publication Data

US 2024/0249021 A1 Jul. 25, 2024

Related U.S. Application Data

(60) Provisional application No. 63/481,431, filed on Jan. 25, 2023.

(51) Int. Cl.

| | |
|---|---|
| ***G06F 21/62*** | (2013.01) |
| ***G06N 3/0475*** | (2023.01) |
| ***G06N 3/091*** | (2023.01) |
| ***G16H 50/20*** | (2018.01) |
| ***G16H 50/70*** | (2018.01) |

(52) U.S. Cl.

CPC ......... *G06F 21/6245* (2013.01); *G06N 3/091* (2023.01); *G06N 3/0475* (2023.01); *G16H 50/20* (2018.01); *G16H 50/70* (2018.01)

(58) Field of Classification Search

CPC .. G06F 21/6245; G06N 3/0475; G16H 50/20; G16H 50/70

See application file for complete search history.

(56) References Cited

U.S. PATENT DOCUMENTS

| | | | |
|---|---|---|---|
| 11,087,025 B2 * | 8/2021 | Santana de Oliveira .................... | G06N 3/02 |
| 2018/0181878 A1 | 6/2018 | Kasiviswanathan et al. | |
| 2023/0129902 A1 | 4/2023 | Park et al. | |
| 2023/0351202 A1 * | 11/2023 | Sakhinana ............. | G06N 3/088 |
| 2024/0211588 A1 * | 6/2024 | Chalk ..................... | G06F 18/10 |

OTHER PUBLICATIONS

Efficient Motif Discovery for Large-Scale Time Series in Healthcare (Year: 2015).*

Esteban C., et al., "Real-Valued (Medical) Time Series Generation with Recurrent Conditional GANs", Dec. 4, 2017, 13 pages, Retrieved from the Internet URL:https://arxiv.org/pdf/1706.02633.pdf.

Frigerio L., et al., "Differentially Private Generative Adversarial Networks for Time Series, Continuous, and Discrete Open Data", March 6, 2019, 18 pages, XP093120114, Retrieved from the Internet URL:https://arxiv.org/pdf/1901.02477.pdf.

International Search Report and Written Opinion for Application No. PCT/US2023/075276, mailed Jan. 29, 2024, 17 pages.

Lamp J., et al., "GlucoSynth: Generating Differentially-Private Synthetic Glucose Traces", Jun. 11, 2023, 27 pages, XP093120034, Retrieved from the Internet: URL:https://arxiv.org/pdf/2303.01621v2.pdf.

* cited by examiner

*Primary Examiner* — Pramila Parthasarathy

(74) *Attorney, Agent, or Firm* — Patterson + Sheridan, LLP

(57) ABSTRACT

A method and system for generating synthetic data is provided. Longitudinal time series data are retrieved, and a neural network is trained to generate synthetic time series data that satisfies a privacy metric based on the longitudinal time series data. The longitudinal time series data are unlabeled and univariate.

19 Claims, 21 Drawing Sheets x
t-5
t-4
t-3
t-2
t-1
t
1206
1205
1204
1203
1202
1201
1200

1215
1213
1211
x1
1220
x4
1224
x2
1222
1221
1230
x5
1234
x3
1233
1232
1210

PRIVATE SYNTHETIC TIME SERIES DATA GENERATION

CROSS-REFERENCE TO RELATED APPLICATIONS

This application claims priority to and benefit of U.S. Provisional Application No. 63/481,431, filed Jan. 25, 2023, which is assigned to the assignee hereof and hereby expressly incorporated herein in its entirety as if fully set forth below and for all applicable purposes.

BACKGROUND

The present disclosure relates to data processing systems. More particularly, the present disclosure relates to private synthetic time series data generation for data processing systems.

Sharing patients' medical longitudinal time series data may enable improved therapy development and technological advances. For example, sharing patients' measured analyte time series data can contribute to the understanding of associated disease mechanisms and the development of technology to improve these patients' qualities of life. Unsurprisingly, there are serious legal and privacy issues that arise when sharing patients' medical longitudinal time series data, such as those described by the Health Insurance Portability and Accountability Act of 1996 (known as HIPAA).

DETAILED DESCRIPTION

Figure 1:
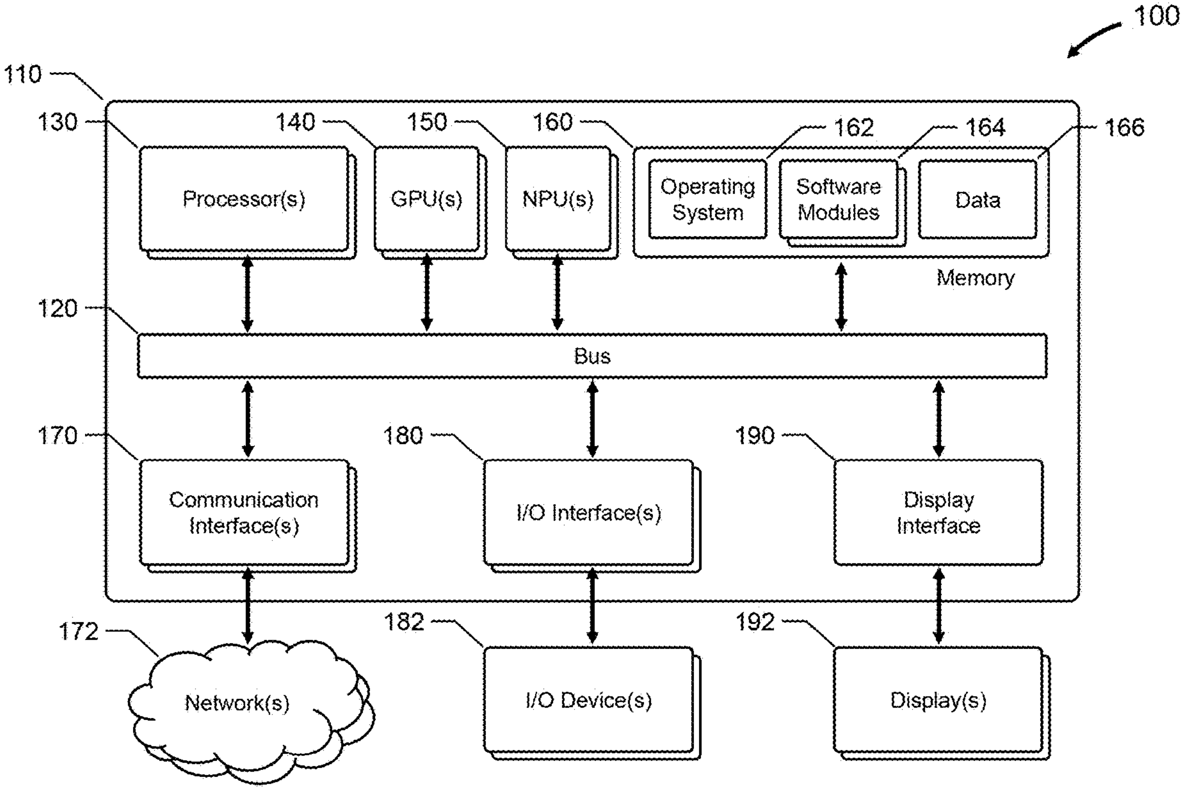
FIG. 1 depicts a block diagram of an example system for generating synthetic data, in accordance with embodiments of the present disclosure.

One potential technical solution to the problem of sharing of patients' medical longitudinal time series data is to generate synthetic (fake) time series data based on the patients' original (real) time series data, such as, for example, a patient's measured glucose traces. However, the synthetic time series data must provide a strong privacy guarantee and protect the privacy of the patients' medical longitudinal time series data while emulating certain important characteristics of the original time series data. A privacy guarantee refers to the degree to which sensitive data, such as a patient's medical data, is protected. A formal notion of a strong privacy guarantee ensures that the probability of disclosing sensitive data is extremely small (e.g., close to zero).

A variety of methodologies may be used to generate synthetic time series data, such as machine learning (ML) techniques, neural networks (NNs), artificial neural networks (ANNs), etc. These methods use training data that may include labels (i.e., labeled data), which are outcomes or labeled parts of the traces that guide the synthetic data generation, or additional information such as multiple variables per time step (i.e., multivariate data), metadata or auxiliary features (information computed during the model training). For example, generative adversarial networks (GANs) may be used to generate synthetic data based on original data. And, while GANs may be trained to generate synthetic time series data based on original time series data, these GANs do not inherently protect the privacy of the original time series data.

Synthetic time series data that protects the privacy of the patients' medical longitudinal time series data may be publicly shared and integrated into many practical applications, such as, for example, blood glucose forecasting, artificial pancreatic systems, computer-based medical diagnostic methodologies, population-level medical studies, etc.

Embodiments of the present disclosure advantageously provide a differential-privacy generative adversarial network (DP-GAN) architecture that includes a motif causality module as well as autoencoder, generator, and discriminator modules. The autoencoder module includes an embedder module and a recovery module. Each module may include, inter alia, one or more ANNs, such as RNNs, LSTM networks, etc., as described below.

Further, embodiments of the present disclosure advantageously provide DP-GAN training methods that include original data, motif data and synthetic data processing techniques, an integrated differential privacy metric, and a loss function that characterizes relationships between important motifs in the original time series data, as described below. A motif is a short, ordered sequence of time steps from a time series (or trace) that characterizes important events in the time series data, such as peaks, troughs, etc. In the context of the present disclosure, motifs are not temporally dependent and do not form recurring temporal patterns.

Importantly, certain embodiments of the present disclosure advantageously relate to training the DP-GAN using unlabeled and univariate original data without any auxiliary (additional) information.

FIG. 1 depicts a block diagram of system 100 for generating synthetic data, in accordance with embodiments of the present disclosure.

Generally, system 100 includes a computer, server, etc., that has one or more single-core or multi-core processors, specialized processors, etc., that are configured to train a neural network, based on longitudinal time series data, to generate synthetic time series data that satisfies a privacy metric.

More particularly, system 100 includes computer 110 coupled to one or more networks 172, one or more I/O devices 182, and one or more displays 192. Computer 110 includes bus 120 coupled to one or more processors 130, storage element or memory 160, one or more communication interfaces 170, one or more I/O interfaces 180, and display interface 190. In many embodiments, computer 110 also includes one or more specialized processors, such as, for example, graphics processing units (GPUs) 140, neural processing units (NPUs) 150, etc. Generally, communication interface(s) 170 are coupled to network(s) 172 using a wired or wireless connection, I/O interface(s) 180 are coupled to I/O device(s) 182 using a wired or wireless connection, and display interface 190 is typically coupled to display(s) 192 using a wired connection.

Bus 120 is a communication system that transfers data between processor(s) 130, memory 160, communication interface(s) 170, I/O interface(s) 180, and display interface 190. In many embodiments, bus 120 also transfers data between these components and GPU(s) 140 and/or NPU(s) 150, as well as other components not depicted in FIG. 1.

Processor(s) 130 include one or more general-purpose or application-specific microprocessors that execute instructions to perform control, computation, input/output, etc. functions for computer 110. Each processor 130 may include a single integrated circuit, such as a micro-processing device, or multiple integrated circuit devices and/or circuit boards working in cooperation to accomplish the appropriate functionality. In addition, processor(s) 130 may execute computer programs or modules, such as operating system 162, software modules 164, etc., stored within memory 160. For example, software modules 164 may include a neural network that includes one or more artificial neural networks (ANNs), recurrent neural networks (RNNs), long short-term memory (LSTM) networks, convolutional neural networks (CNNs), etc.

Generally, memory 160 stores instructions for execution by processor(s) 130 as well as data. Memory 160 may include a variety of non-transitory computer-readable medium that may be accessed by processor(s) 130 as well as other components. In various embodiments, memory 160 may include volatile and nonvolatile medium, non-removable medium and/or removable medium. For example, memory 160 may include any combination of random access memory (RAM), dynamic RAM (DRAM), static RAM (SRAM), read only memory (ROM), flash memory, cache memory, and/or any other type of non-transitory computer-readable medium.

Memory 160 contains various components for retrieving, presenting, modifying, and storing data 166. For example, memory 160 stores software modules 164 that provide functionality when executed by processor(s) 130. Operating system 162 provides operating system functionality for computer 110. Software modules 164 provide various functionality, as described above. Data 166 may include data associated with operating system 162, software modules 164, etc.

Communication interface(s) 170 are configured to transmit data to and from one or more network(s) 172 using one or more wired and/or wireless connections. Network(s) 172 may include one or more local area networks, wide area networks, the Internet, etc., which may execute various network protocols, such as, for example, wired and/or wireless Ethernet, Bluetooth, etc. Network(s) 172 may also include various combinations of wired and/or wireless physical layers, such as, for example, copper wire or coaxial cable networks, fiber optic networks, Bluetooth wireless networks, WiFi wireless networks, CDMA, FDMA and TDMA cellular wireless networks, etc.

I/O interface(s) 180 are configured to transmit and/or receive data from I/O device(s) 182. I/O interface(s) 180 enable connectivity between processor(s) 130, memory 160 and I/O device(s) 182 by encoding data to be sent from processor 130 or memory 160 to I/O device(s) 182, and decoding data received from I/O device(s) 182 for processor(s) 130 or memory 160. Generally, data may be sent over wired and/or wireless connections. For example, I/O interface(s) 180 may include one or more wired communications interfaces, such as USB, Ethernet, etc., and/or one or more wireless communications interfaces, coupled to one or more antennas, such as WiFi, Bluetooth, cellular, etc.

Generally, I/O device(s) 182 provide input to computer 110 and/or output from computer 110. As discussed above, I/O device(s) 182 are operably connected to computer 110 using a wired and/or wireless connection. I/O device(s) 182 may include a local processor coupled to a communication interface that is configured to communicate with computer 110 using the wired and/or wireless connection. For example, I/O device(s) 182 may include a keyboard, mouse, touch pad, joystick, etc.

Display interface 190 is configured to transmit image data from computer 110 to monitor or display 192.

As noted above, software modules 164 may include a neural network that includes one or more ANNs, RNNs, LSTMs, etc.

An ANN models the relationships between input data or signals and output data or signals using a network of interconnected nodes that is trained through a learning process. The nodes are arranged into various layers, including, for example, an input layer, one or more hidden layers, and an output layer. The input layer receives input data, such as, for example, image data, sensor time series data, etc., and the output layer generates output data, such as, for example, a probability that the image data contains a known object, a medical condition, etc. Each hidden layer provides at least a partial transformation of the input data to the output data. A DNN has multiple hidden layers in order to model complex, nonlinear relationships between input data and output data.

In a fully-connected, feedforward ANN, each node is connected to all of the nodes in the preceding layer, as well as to all of the nodes in the subsequent layer. For example, each input layer node is connected to each hidden layer node, each hidden layer node is connected to each input layer node and each output layer node, and each output layer node is connected to each hidden layer node. Additional hidden layers are similarly interconnected. Each connection has a weight value, and each node has an activation function, such as, for example, a linear function, a step function, a sigmoid function, a hyperbolic or tanh operation, a rectified linear unit (ReLu) function, etc., that determines the output of the node based on the weighted sum of the inputs to the node. The input data propagates from the input layer nodes, through respective connection weights to the hidden layer nodes, and then through respective connection weights to the output layer nodes. The sigmoid and ReLu functions output a number between 0 and 1, while the tanh operation outputs a number between −1 and 1, for any given input.

More particularly, at each input node, input data is provided to the activation function for that node, and the output of the activation function is then provided as an input data value to each hidden layer node. At each hidden layer node, the input data value received from each input layer node is multiplied by a respective connection weight, and the resulting products are summed or accumulated into an activation signal value that is provided to the activation function for that node. The output of the activation function is then provided as an input data value to each output layer node. At each output layer node, the output data value received from each hidden layer node is multiplied by a respective connection weight, and the resulting products are summed or accumulated into an activation signal value that is provided to the activation function for that node. The output of the activation function is then provided as output data. Additional hidden layers may be similarly configured to process data.

Figure 2:
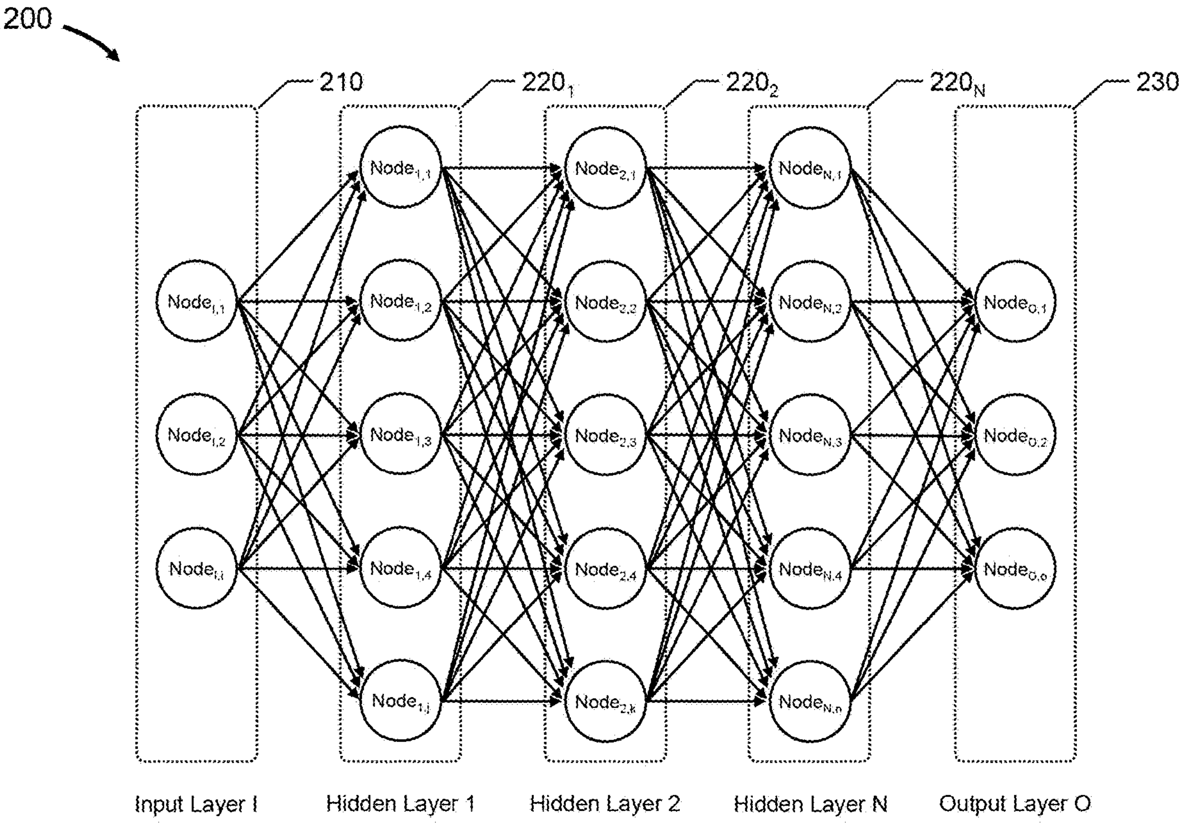
FIG. 2 depicts an example artificial neural network (ANN), in accordance with embodiments of the present disclosure.

FIG. 2 depicts ANN 200, in accordance with embodiments of the present disclosure.

ANN 200 includes input layer 210, one or more hidden layers, e.g., hidden layers $\mathbf{210}_1$, $\mathbf{220}_2$, . . . , $\mathbf{220}_N$, and output layer 230. Input layer 210 includes one or more input nodes, e.g., $\text{Node}_{1,1}$, $\text{Node}_{1,2}$, . . . , $\text{Node}_{1,i}$. Hidden layer 2201 includes one or more hidden nodes, e.g., $\text{Node}_{1,1}$, $\text{Node}_{1,2}$, . . . , $\text{Node}_{1,j}$. Hidden layer $\mathbf{220}_2$ includes one or more hidden nodes, e.g., $\text{Node}_{2,1}$, $\text{Node}_{2,2}$, . . . , $\text{Node}_{2,k}$. Hidden layer $\mathbf{220}_N$ includes one or more hidden nodes, e.g., $\text{Node}_{N,1}$, $\text{Node}_{N,2}$, . . . , $\text{Node}_{N,n}$. Output layer 230 includes one or more output nodes, e.g., $\text{Node}_{O,1}$, $\text{Node}_{O,2}$, . . . , $\text{Node}_{O,o}$. In the example depicted in FIG. 2, there are N hidden layers; input layer 210 includes "i" nodes, hidden layer 2301 includes "j" nodes, hidden layer $\mathbf{220}_2$ includes "k" nodes, hidden layer 230N includes "n" nodes, and output layer 230 includes "o" nodes.

In certain embodiments, N equals 3, "i" equals 3, "j", "k" and "n" equal 5 and "o" equals 3. Input $\text{Node}_{1,1}$, $\text{Node}_{1,2}$ and $\text{Node}_{1,3}$ are each coupled to hidden $\text{Node}_{1,1}$, $\text{Node}_{1,2}$, $\text{Node}_{1,3}$, $\text{Node}_{1,4}$ and $\text{Node}_{1,5}$. Hidden $\text{Node}_{1,1}$, $\text{Node}_{1,2}$, $\text{Node}_{1,3}$, $\text{Node}_{1,4}$ and $\text{Node}_{1,5}$ are each coupled to hidden $\text{Node}_{2,1}$, $\text{Node}_{2,2}$, $\text{Node}_{2,3}$, $\text{Node}_{2,4}$ and $\text{Node}_{2,5}$. Hidden $\text{Node}_{2,1}$, $\text{Node}_{2,2}$, $\text{Node}_{2,3}$, $\text{Node}_{2,4}$ and $\text{Node}_{2,5}$ are each coupled to hidden $\text{Node}_{3,1}$, $\text{Node}_{3,2}$, $\text{Node}_{3,3}$, $\text{Node}_{3,4}$ and $\text{Node}_{3,5}$. Hidden $\text{Node}_{3,1}$, $\text{Node}_{3,2}$, $\text{Node}_{3,3}$, $\text{Node}_{3,4}$ and $\text{Node}_{3,5}$ are each coupled to output $\text{Node}_{0,1}$, $\text{Node}_{O,2}$, $\text{Node}_{O,3}$.

Many other variations of input, hidden and output layers are clearly possible, including hidden layers that are locally-connected, rather than fully-connected, to one another.

Training an ANN includes optimizing the connection weights between nodes by minimizing the prediction error of the output data until the ANN achieves a particular level of accuracy. One method is backpropagation, or backward propagation of errors, which iteratively and recursively determines a gradient (i.e., a partial derivative of the error function) with respect to each weight, and then adjusts each weight to improve the performance of the network.

A multi-layer perceptron (MLP) is a fully-connected ANN that has an input layer, an output layer and one or more hidden layers. MLPs may be used for processing time series data, such as natural language processing, machine translation, speech recognition, etc. Other ANNs include RNNs, LSTM networks, CNNs, etc.

Figures 3A, 3B:
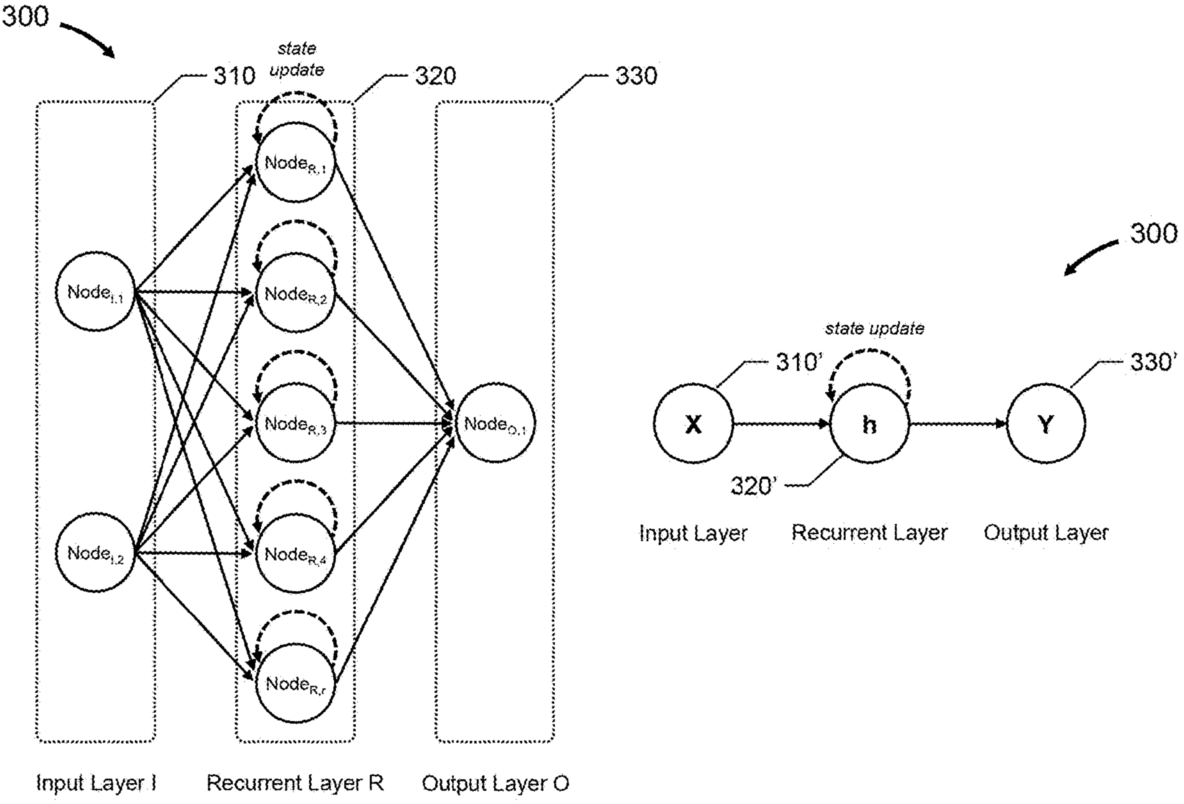
FIGS. 3A, 3B, 3C and 3D depict different views of an example recurrent neural network (RNN), in accordance with embodiments of the present disclosure.

FIG. 3A depicts one view of RNN 300, in accordance with embodiments of the present disclosure.

Generally, RNNs process input sequence data and generate output sequence data, and may be used for many different applications, such as, for example, natural language processing applications (e.g., sentiment analysis, speech recognition, reading comprehension, summarization and translation, etc.), image processing (e.g., image captioning, video classification, etc.), etc. RNNs may be programmed to process many different types of input and output data, such as, for example, fixed input data and fixed output data for image classification, etc., fixed input data and sequential output data for image captioning, etc., sequential input data and fixed output data for sentence "sentiment" classification, etc., sequential input data and sequential output data for machine translation, etc., synced sequential input data and sequential output data for video classification, etc.

RNN 300 includes input layer 310, one or more hidden layers, such as hidden recurrent layer 320, and output layer 330. Generally, an RNN may include one to four hidden recurrent layers; other numbers of hidden recurrent layers are also supported.

Input layer 310 includes one or more input nodes, such as $\text{Node}_{1,1}$ and $\text{Node}_{1,2}$, that present the input data X to hidden recurrent layer 320 as sequences of input data values, such as, for example, sequences of letters, words, sentences, etc., sequences of measured data values, sensor data values, etc. Generally, each sequence is a time step, and the input data are processed as vectors or matrices. RNN 300 processes the input data values for each time step, and typically executes a loop to process the total number of time steps.

Hidden recurrent layer 320 is a fully connected, recurrent layer that includes hidden recurrent nodes, such as, for example, $\text{Node}_{R,1}$, $\text{Node}_{R,2}$, $\text{Node}_{R,3}$, $\text{Node}_{R,4}$, . . . , $\text{Node}_{R,r}$. Each hidden recurrent node maintains or stores a state for a hidden state vector h for this layer, which is updated at each time step of RNN 300. In other words, the hidden state vector h includes a state for each hidden recurrent node in hidden recurrent layer 320. In many embodiments, the size of the hidden state vector h ranges from tens or hundreds to a few thousand elements, such as, for example, 64, 256, 4,096, etc. elements. In certain embodiments, the hidden state vector h may be subsampled to reduce processing requirements.

One or more additional, fully-connected, hidden recurrent layers may follow hidden recurrent layer 320. Each successive, hidden recurrent layer includes hidden recurrent nodes and a corresponding hidden state vector h. The last hidden layer, e.g., hidden recurrent layer 320 depicted in FIG. 3A, presents the hidden state vector h to output layer 330.

Output layer 330 is a fully-connected layer that includes one or more output nodes, e.g., $Node_{0,1}$, that generate the output data Y. In certain embodiments, each output node provides an output, such as a predicted class score, probability of a word, sentence, etc., predicted data value, predicted correlation value, etc. A normalization function, such as a Softmax function, may be applied to the output by output layer 330, or, alternatively, by an additional fully-connected layer interposed between the last hidden layer and output layer 330.

FIG. 3B depicts another view of RNN 300, in accordance with embodiments of the present disclosure.

Input layer 310 is depicted as a single element 310' including the input data X, hidden recurrent layer 320 is depicted as a single element, module or cell 320' including the hidden state vector h, and output layer 330 is depicted as a single element 330' including the output data Y.

Figures 3C, 3D:
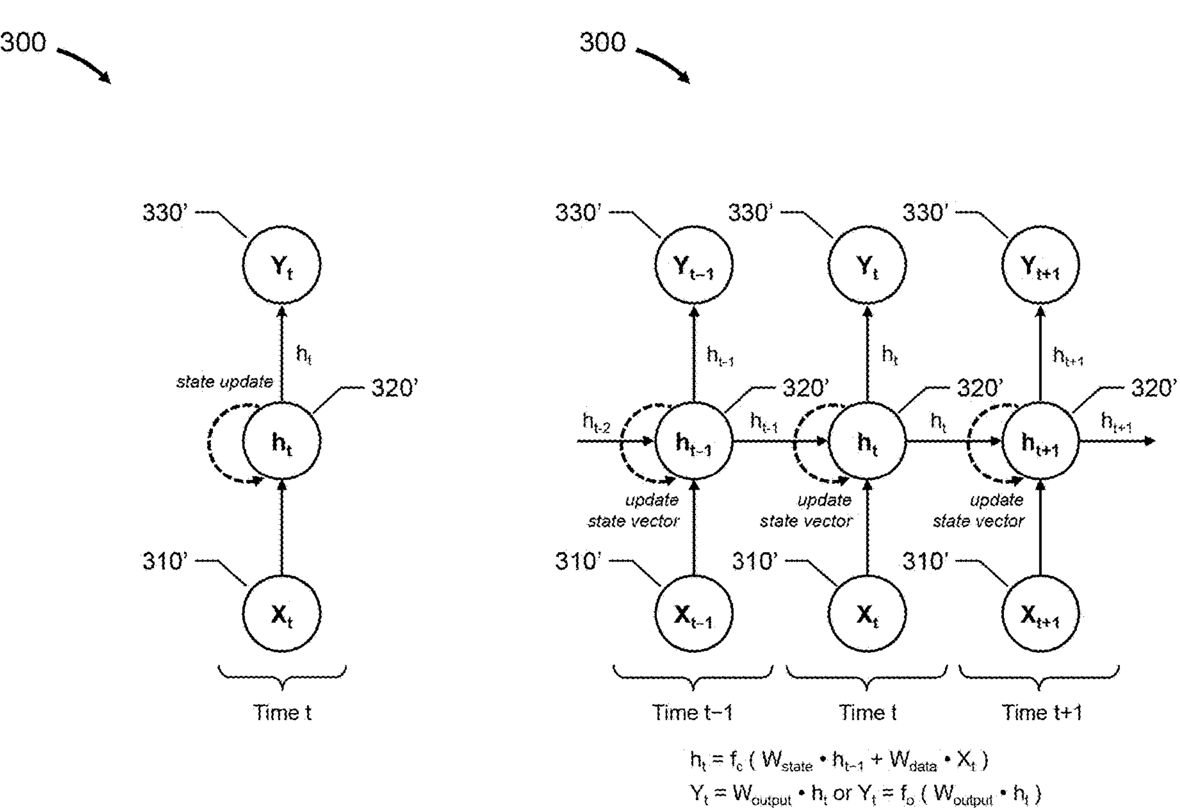

FIG. 3C depicts another view of RNN 300, in accordance with embodiments of the present disclosure.

The view of RNN 300 depicted in FIG. 3B has been rotated and annotated to indicate the processing configuration of RNN 300 at time step t, i.e., input layer 310' including the input data $X_t$, hidden recurrent module 320' including the hidden state vector $h_t$, and output layer 330' including the output data $Y_t$. In many embodiments, input data $X_t$ is a vector having the same dimension as hidden state vector $h_t$.

FIG. 3D depicts another view of RNN 300, in accordance with embodiments of the present disclosure.

As noted above, RNN 300 typically executes a loop so that hidden recurrent module 320' may process the input data X and update the hidden state vector h at each time step. In the view depicted in FIG. 3D, the loop has been "unrolled" and three time steps are shown, i.e., t−1, t and t+1. Accordingly, RNN 300 may be viewed as a chain of repeating hidden recurrent modules or cells 320'.

At time step t−1, the input data $X_{t-1}$, the input hidden state vector $h_{t-2}$ from the previous time step, the hidden state vector $h_{t-1}$, and the output data $Y_{t-1}$ are shown. At time step t, the input data $X_t$, the input hidden state vector $h_{t-1}$ from the previous time step, the hidden state vector $h_t$, and the output data $Y_t$ are shown. At time step t+1, the input data $X_{t+1}$, the input hidden state vector $h_t$ from the previous time step, the hidden state vector $h_t+1$, and the output data $Y_t+1$ are shown.

Generally, the hidden state vector $h_t$ may be updated by applying an activation function fc to the sum of a weight vector $W_{state}$ multiplied by the hidden state vector $h_{t-1}$ from the previous time step, and a weight vector $W_{data}$ multiplied by the input data $X_t$, as given by Equation 1.

$$h_t = f_c(W_{state} \cdot h_{t-1} + W_{data} \cdot X_t) \quad \text{Eq. 1}$$

The activation function $f_c$ may be a non-linear activation function, such as, for example, tanh( ) ReLu, etc., applied to each element of the hidden state vector h. In certain embodiments, a bias $b_c$ may be added to the sum prior to the application of the activation function $f_c$. The output data $Y_t$ is the product of a weight vector $W_{output}$ multiplied by the hidden state vector $h_t$, as given by Equation 2.

$$Y_t = W_{output} \cdot h_t \quad \text{Eq. 2}$$

In certain embodiments, an activation function $f_o$ may be applied to the product of the weight vector $W_{output}$ and the hidden state vector $h_t$, such as, for example, tanh( ) ReLu, etc., to generate the output data $Y_t$, as given by Equation 3.

$$Y_t = f_o(W_{output} \cdot h_t) \quad \text{Eq. 3}$$

In certain embodiments, a bias $b_o$ may be added to the product prior to the application of the activation function $f_o$.

Figure 3E:
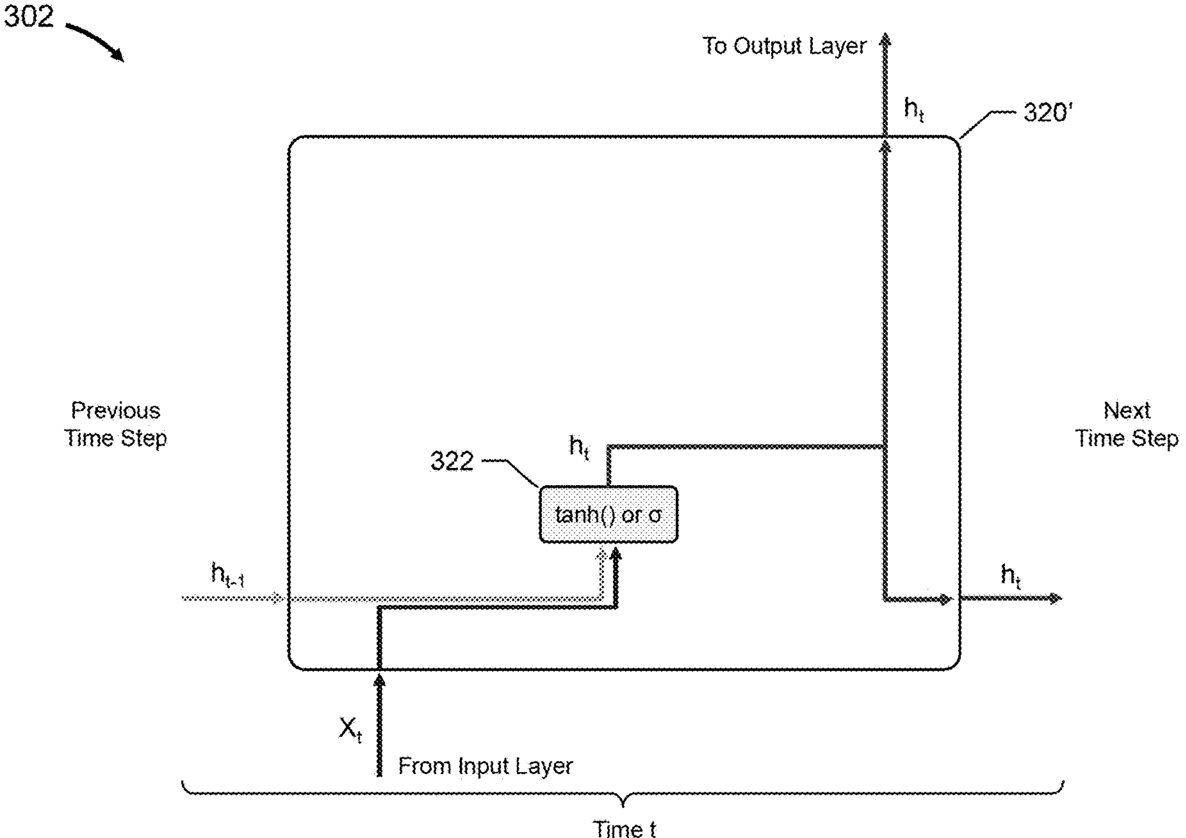
FIG. 3E depicts an example data flow diagram for a hidden recurrent module, in accordance with embodiments of the present disclosure.

FIG. 3E depicts a data flow diagram 302 for hidden recurrent module 320', in accordance with embodiments of the present disclosure.

Hidden recurrent module 320' is shown at time step t. Hidden recurrent module 320' includes tanh or sigmoid layer 322, which receives hidden state vector $h_{t-1}$ and input data vector $X_t$, applies a tanh operation to the sum of the weight vector $W_{state}$ multiplied by the hidden state vector $h_{t-1}$ from the previous time step, and the weight vector $W_{data}$ multiplied by the input data $X_t$, to generate hidden state vector $h_t$, as given by Equation 1. The hidden state vector $h_t$ is output to output layer 330, and provided to, or stored for use by, the next time step.

Similar to ANNs, training an RNN includes optimizing the weights by minimizing the prediction error of the output data until the RNN achieves a particular level of accuracy. As noted above, backpropagation through time may be used to iteratively and recursively determine a gradient (i.e., a partial derivative of the error function) with respect to each weight, and then adjust each weight to improve the performance of the RNN. However, when the gradient for one or more of the weights becomes too small (i.e., when the gradient "vanishes"), these weights are not adjusted and training eventually stops. This issue is known as the vanishing gradient problem.

An LSTM network is a variation of an RNN that, among other advantages, addresses the vanishing gradient problem by increasing the complexity of each hidden recurrent module or cell in order to generate and maintain more information than just the hidden state vector h, i.e., a cell state vector C. LSTM networks also avoid the RNN's long-term dependency problem.

Figures 4A, 4B:
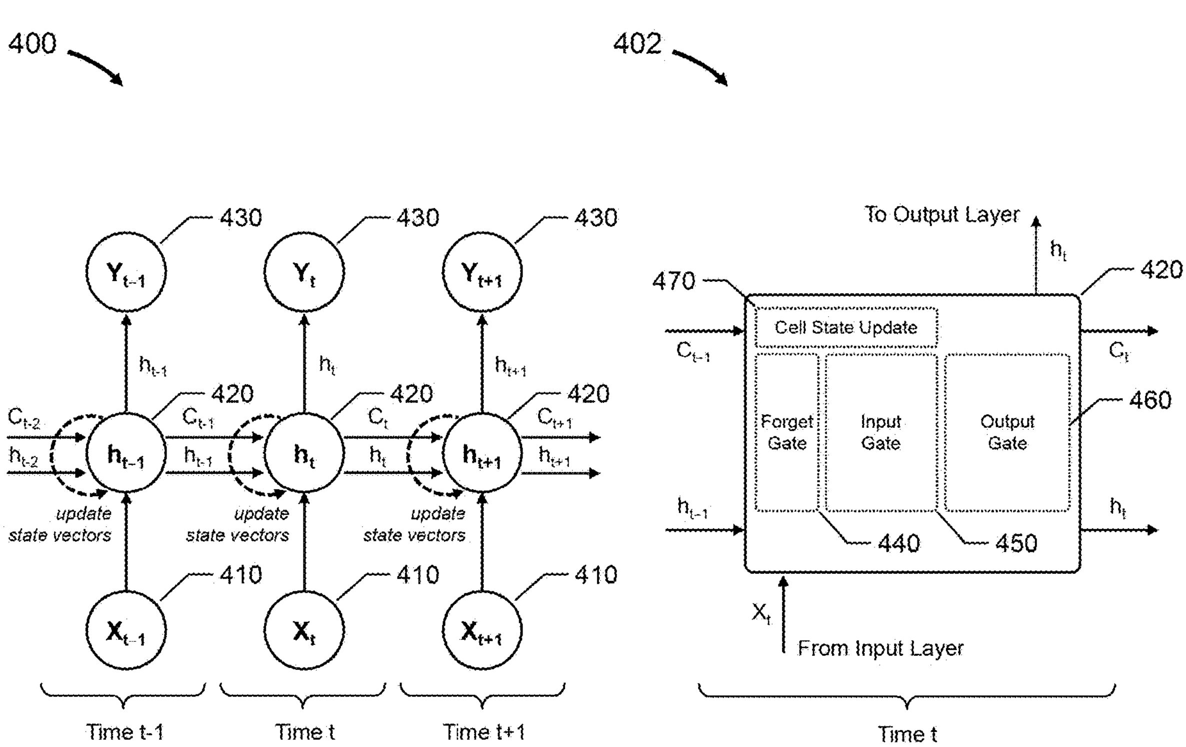
FIG. 4A depicts a view of an example long short-term memory (LSTM) network, in accordance with embodiments of the present disclosure.
FIGS. 4B and 4C depict example data flow diagrams for an LSTM cell, in accordance with embodiments of the present disclosure.

FIG. 4A depicts a view of LSTM network 400, in accordance with embodiments of the present disclosure.

LSTM network 400 also typically executes a loop so that LSTM module or cell 420 may process each time step. In the view depicted in FIG. 4A, the loop has been "unrolled" and three time steps are shown, similar to the view of RNN 300 depicted in FIG. 3D. Accordingly, LSTM network 400 may also be viewed as a chain of repeating LSTM cells 420.

At time step t−1, the input data $X_{t-1}$, the input hidden state vector $h_{t-2}$ and the input cell state vector $C_{t-2}$ from the previous time step, the hidden state vector $h_{t-1}$, the cell state vector $C_{t-1}$, and the output data $Y_{t-1}$ are shown. At time step t, the input data $X_t$, the input hidden state vector $h_{t-1}$ and the input cell state vector $C_{t-1}$ from the previous time step, the hidden state vector $h_t$, the cell state vector $C_t$, and the output data $Y_t$ are shown. At time step t+1, the input data $X_t+1$, the input hidden state vector $h_t$ and the input cell state vector $C_t$ from the previous time step, the hidden state vector $h_{t+1}$, the cell state vector $C_{t+1}$, and the output data $Y_{t+1}$ are shown.

FIG. 4B depicts a data flow diagram 402 of LSTM cell 420, in accordance with embodiments of the present disclosure.

LSTM cell 420 is shown at time step t. LSTM cell 420 receives or retrieves cell state vector $C_{t-1}$ and hidden state vector $h_{t-1}$ from the previous time step, receives input data $X_t$ from input layer 410 for the current time step, processes these data to generate the cell state vector $C_t$ and the hidden state vector $h_t$ for the current time step, sends the hidden state vector $h_t$ for the current time step to output layer 430, and sends or stores the hidden state vector $h_t$ and the cell state vector $C_t$ for the next time step.

LSTM cell 420 includes, inter alia, cell storage (not shown for clarity), forget gate 440, input gate 450, output gate 460, and cell state update segment 470. LSTM cell 420 may be implemented by software modules, processes, routines, etc., by hardware components, circuits, etc., by a combination of hardware and software components, etc.

Forget gate 440 determines which elements of the cell state vector $C_{t-1}$ should be discarded (i.e., "forgotten") or kept (i.e., "remembered") based on the hidden state vector $h_{t-1}$ and the input data $X_t$. Input gate 450 generates new information to be added to the cell state vector $C_{t-1}$ based on the hidden state vector $h_{t-1}$ and the input data $X_t$. Cell state update segment 470 updates the cell state vector $C_{t-1}$, based on the output of forget gate 440 and input gate 450, to generate the cell state vector $C_t$. Output gate 460 generates the hidden state vector $h_t$ based on the hidden state vector $h_{t-1}$, the input data $X_t$ and the updated cell state vector $C_t$.

Figure 4C:
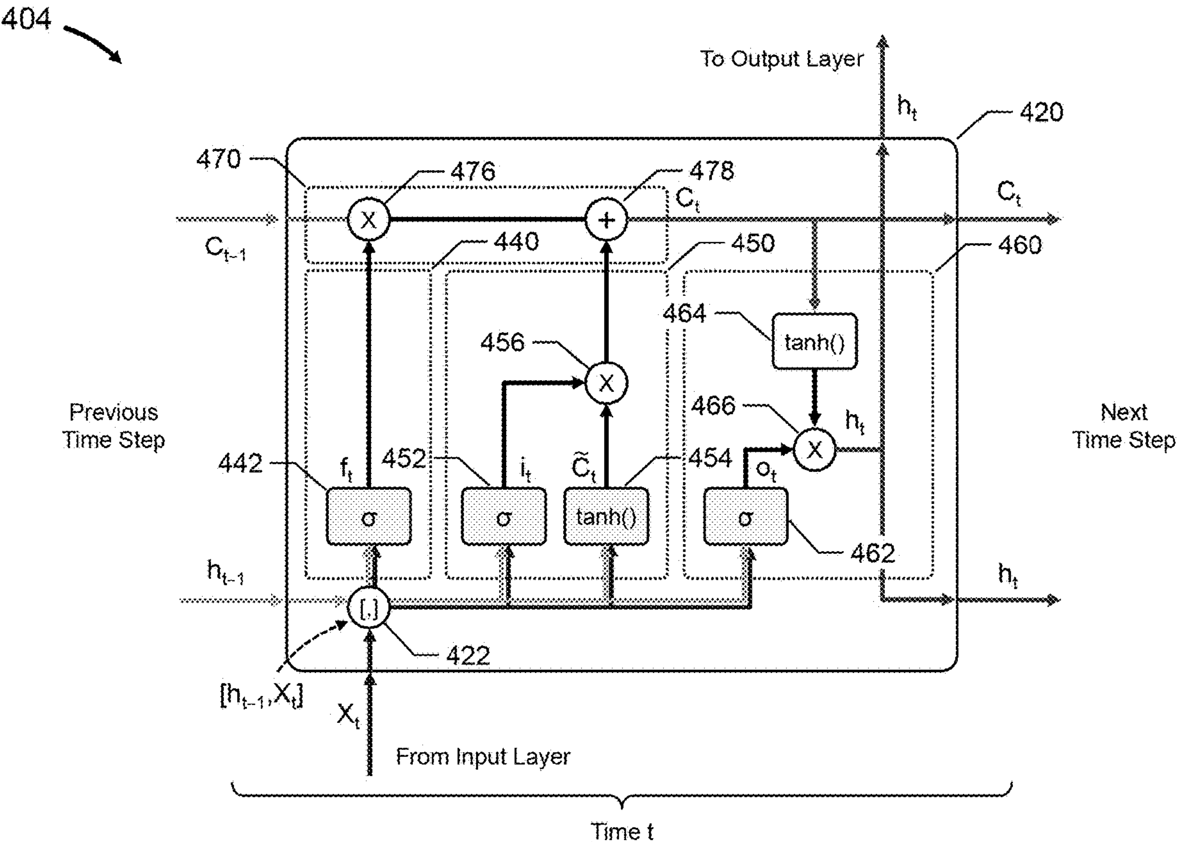

FIG. 4C depicts a data flow diagram 404 for LSTM cell 420, in accordance with embodiments of the present disclosure.

LSTM cell 420 is shown at time step t. Hidden state vector $h_{t-1}$ and input data vector $X_t$ are provided to forget gate 440, input gate 450, and output gate 460. In many embodiments, concatenation operation 422 concatenates the hidden state vector $h_{t-1}$ and input data vector $X_t$ to form a concatenated input vector $[h_{t-1}, X_t]$, which is provided to forget gate 440, input gate 450, and output gate 460. In other embodiments, the hidden state vector $h_{t-1}$ and input data vector $X_t$ are provided separately to forget gate 440, input gate 450, and output gate 460.

Forget gate 440 includes sigmoid layer 442, which receives the concatenated input vector $[h_{t-1}, X_t]$ from concatenation operation 422, applies a concatenated weight vector $W_f$ to the concatenated input vector $[h_{t-1}, X_t]$ to generate a weighted concatenated input vector $W_f \cdot [h_{t-1}, X_t]$, and applies the sigmoid function to the weighted concatenated input vector $W_f \cdot [h_{t-1}, X_t]$ to generate the activation vector $f_t$, as given by Equation 4. The concatenated weight vector $W_f$ is a concatenation of a weight vector for the hidden state vector $h_{t-1}$ and a weight vector for the input data vector $X_t$.

$$f_t = \sigma(W_f \cdot [h_{t-1}, X_t]) \quad \text{Eq. 4}$$

In certain embodiments, a bias $b_f$ may be added to the weighted concatenated input vector $W_f \cdot [h_{t-1}, X_t]$ prior to the application of the sigmoid function σ. Sigmoid layer 442 provides the activation vector $f_t$ to element-wise multiplication operation 476 within cell state update segment 470.

Input gate 450 includes sigmoid layer 452, tanh layer 454 and element-wise multiplication operation 456. Sigmoid layer 452 receives the concatenated input vector $[h_{t-1}, X_t]$ from concatenation operation 422, applies a concatenated weight vector $W_i$ to the concatenated input vector $[h_{t-1}, X_t]$ to generate a weighted concatenated input vector $W_i \cdot [h_{t-1}, X_t]$, and applies the sigmoid function to the weighted concatenated input vector $W_i \cdot [h_{t-1}, X_t]$ to the generate activation vector it, as given by Equation 5.

$$i_t = \sigma(W_i \cdot [h_{t-1}, X_t]) \quad \text{Eq. 5}$$

In certain embodiments, a bias bi may be added to the weighted concatenated input vector $W_i \cdot [h_{t-1}, X_t]$ prior to the application of the sigmoid function σ. Sigmoid layer 452 provides the activation vector it to element-wise multiplication operation 456.

Tanh layer 454 receives the concatenated input vector $[h_{t-1}, X_t]$ from concatenation operation 422, applies a concatenated weight vector $W_C$ to the concatenated input vector $[h_{t-1}, X_t]$ to generate a weighted concatenated input vector $W_C \cdot [h_{t-1}, X_t]$, and applies the tanh operation to the weighted concatenated input vector $W_C \cdot [h_{t-1}, X_t]$ to generate activation vector $\tilde{C}_t$, as given by Equation 6.

$$\tilde{C}_t = \tanh(W_C \cdot [h_{t-1}, X_t]) \quad \text{Eq. 6}$$

In certain embodiments, a bias $b_C$ may be added to the weighted concatenated input vector $W_C \cdot [h_{t-1}, X_t]$ prior to the application of the tanh operation. Tanh layer 454 provides the activation vector $\tilde{C}_t$ to element-wise multiplication operation 456. Element-wise multiplication operation 456 multiplies the activation vector it and the activation vector $C_t$ to generate an intermediate product, which is provided to element-wise addition operation 478 within cell state update segment 470.

Output gate 460 includes sigmoid layer 462, element-wise multiplication operation 466, and element-wise tanh operation 464. Sigmoid layer 462 receives the concatenated input vector $[h_{t-1}, X_t]$ from concatenation operation 422, applies a concatenated weight vector $W_o$ to the concatenated input vector $[h_{t-1}, X_t]$ to generate a weighted concatenated output vector $W_o \cdot [h_{t-1}, X_t]$, and applies the sigmoid function to the weighted concatenated output vector $W_o \cdot [h_{t-1}, X_t]$ to generate activation vector $o_t$, as given by Equation 7.

$$o_t = \sigma(W_o \cdot [h_{t-1}, X_t]) \quad \text{Eq. 7}$$

In certain embodiments, a bias $b_o$ may be added to the weighted concatenated input vector $W_o \cdot [h_{t-1}, X_t]$ prior to the application of the sigmoid function σ. Sigmoid layer 462 provides the activation vector $o_t$ to element-wise multiplication operation 466.

Tanh operation 464 receives the cell state vector $C_t$, applies the tanh operation to the cell state vector $C_t$, and provides the result to element-wise multiplication operation 466, which multiplies the outputs of sigmoid layer 462 and tanh operation 464 to generate the hidden state vector $h_t$, as given by Equation 8.

$$h_t = o_t \cdot \tanh(C_t) \quad \text{Eq. 8}$$

Element-wise multiplication operation 476 within cell state update segment 470 receives the cell state vector $C_{t-1}$, and multiplies activation vector $f_t$ and cell state vector $C_{t-1}$ to generate an intermediate vector product, which is provided to element-wise addition operation 478. The intermediate vector product generated by element-wise multiplication operation 476 and element-wise multiplication operation 456 are added together to generate the cell state vector $C_t$, as given by Equation 9.

$$C_t = f_t \cdot C_{t-1} + i_t \cdot \tilde{C}_t \quad \text{Eq. 9}$$

The hidden state vector $h_t$ is output to output layer 430. The hidden state vector $h_t$ and the cell state vector $C_t$ are provided to, or stored for use by, the next time step.

Figure 5:
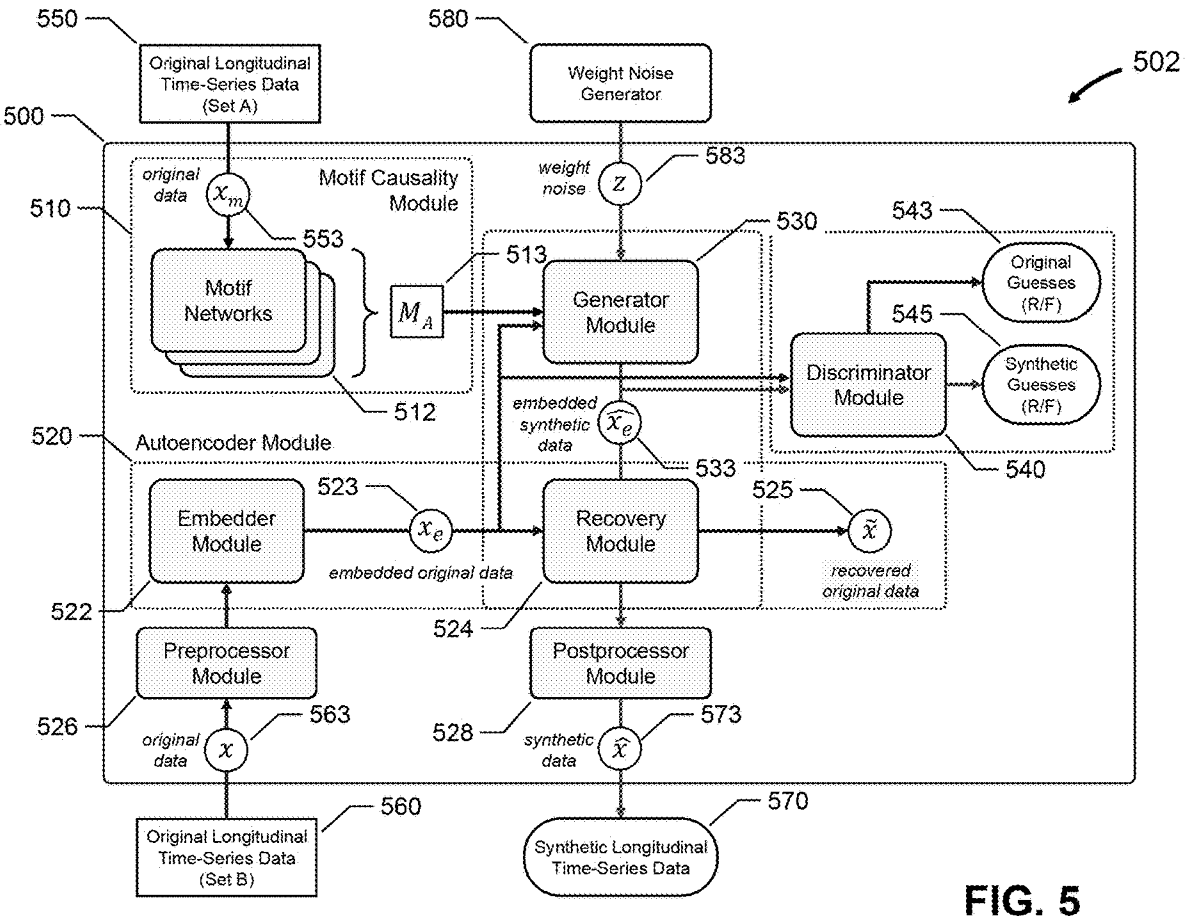
FIG. 5 depicts an example data flow diagram for a differential-privacy generative adversarial network (DP-GAN), in accordance with embodiments of the present disclosure.

FIG. 5 depicts a data flow diagram 502 for DP-GAN 500, in accordance with embodiments of the present disclosure.

As noted above, GANs may be used to generate synthetic data based on original data. Generally, GANs include a generator neural network and a discriminator neural network. The generator neural network learns from the original data and works to generate synthetic data. The discriminator neural network receives samples of both original (real) data and synthetic (fake) data, and "guesses" whether each sample is real or fake. The generator neural network and the discriminator neural network are trained adversarially, i.e., against each other. The generator neural network attempts to fool the discriminator neural network into guessing that the synthetic data is real, and the discriminator neural network attempts to become very good at guessing which samples are actually real or fake. When the training is successful, the generator neural network becomes very good at generating synthetic data that fools the discriminator neural network into guessing that the synthetic data is real.

Differential privacy is a formal notion of privacy that bounds the risk to any person who provides data for subsequent processing. In a DP-GAN, noise is drawn from carefully designed distributions and applied to the weights of the generator neural network and the discriminator neural network to protect the privacy of the individuals associated with the data. From one perspective, the addition of noise prevents the DP-GAN's generator and discriminator neural networks from memorizing or disclosing any sensitive or personal information from the original data.

DP-GAN 500 includes motif causality module 510, autoencoder module 520, generator module 530, discriminator module 540, preprocessor module 526 and postprocessor module 528. Autoencoder module 520 includes embedder module 522 and recovery module 524. Each module may include, inter alia, one or more neural networks, such as RNNs, LSTM networks, etc., implemented as software modules, processes, routines, etc. In many embodiments, these software components may be executed by processor(s) 130. In certain embodiments, at least a portion of these software components may be executed by GPU 140 or NPU 150. In other embodiments, these software components may be executed by a combination of processor 130 and GPU 140, processor 130 and NPU 150, or processor 130, GPU 140 and NPU 150.

In many embodiments, medical longitudinal time series data (traces) for a population of patients (persons) may be divided into two sets, i.e., set A and set B. Each set includes a number of traces for a different group of patients (persons) within the population. Set A may include the same number of traces as set B, set A may include less traces than set B, or set A may include more traces than set B. In certain embodiments, the medical longitudinal time series data may be entirely divided into set A and set B, while in other embodiments, the medical longitudinal time series data may be partially divided into set A and set B based upon a selection criteria. For example, a patient's medical longitudinal time series data may be selected based on quality. As an example, un-selected patient medical longitudinal time series data may exhibit undesirable characteristics such as measurement noise, data dropouts, etc. Generally, a patient's medical longitudinal time series data are bounded and include at least 50 time steps. Certain medical longitudinal time series data may include 100 or more time steps, such as, for example, 288 time steps for 24 hours of continuous glucose monitoring (CGM) data (i.e., 12 measurements/hour).

Original longitudinal time series data (set A) 550 are provided to motif causality module 510 as original data $x_m$ (data 553). Original longitudinal time series data (set B) 560 are provided to preprocessor module 526 as original data x (data 563).

Motif causality module 510 includes a data processing module (not shown for clarity) that processes original data $x_m$ to generate a number of non-overlapping motif data partitions. Each motif data partition is provided to a different motif network 512. Each motif network 512 generates a motif causality matrix $M_i$, which are aggregated into aggregated motif causality matrix $M_A$ and provided to generator module 530. During training, motif networks 512 learn the relationships amongst motifs and express these relationships in causality matrices, which are aggregated into an aggregated motif causality matrix $M_A$ to preserve patient privacy. Motif causality module 510 is discussed in more detail below.

Preprocessor module 526 preprocesses original data x to generate batched original data x, and provides the batched original data x to embedder module 522.

Embedder module 522 reduces the dimensionality of the batched original data x to generate an embedded set of traces, i.e., embedded original data $x_e$ (data 523). In many embodiments, embedder module 522 includes a neural network with an input layer, at least one hidden layer, such as, for example, an RNN layer (e.g., hidden recurrent layer 320, hidden recurrent module 320', etc.) or LSTM layer (e.g., LSTM cell 420, etc.), and an output layer. In certain embodiments, the neural network may be a CNN. Other neural network architectures are also supported.

Generator module 530 generates embedded synthetic data $\hat{x}_e$ (data 533) based on embedded original data $x_e$ and aggregated motif causality matrix 513 ($M_A$). In many embodiments, generator module 530 includes a neural network with an input layer, at least one hidden layer, such as, for example, an RNN layer (e.g., hidden recurrent layer 320, hidden recurrent module 320', etc.) or LSTM layer (e.g., LSTM cell 420, etc.), and an output layer. Other neural network architectures are also supported.

Postprocessor module 528 reconstructs the embedded synthetic data $\widehat{x_e}$ in the original data space to generate synthetic data $\hat{x}$ (data 573), which may be output as synthetic longitudinal time series data 570.

Recovery module 524 reconstructs the embedded original data $x_e$ in the original data space to generate recovered original data % (data 525). In many embodiments, recovery module 524 includes a neural network with an input layer, at least one hidden layer, such as, for example, an RNN layer (e.g., hidden recurrent layer 320, hidden recurrent module 320', etc.) or LSTM layer (e.g., LSTM cell 420, etc.), and an output layer. In certain embodiments, the neural network may be a CNN. Other neural network architectures are also supported.

Discriminator module 540 receives the embedded original data $x_e$ and guesses whether the embedded original data $x_e$ is real or fake. Similarly, discriminator module 540 also receives the embedded synthetic data $\widehat{x_e}$ and guesses whether the embedded synthetic data $\widehat{x_e}$ is real or fake. The guesses may be output as embedded original guesses 543 and embedded synthetic guesses 545. In many embodiments, discriminator module 540 includes a neural network with an input layer, at least one hidden layer, such as, for example, an RNN layer (e.g., hidden recurrent layer 320, hidden recurrent module 320', etc.) or LSTM layer (e.g., LSTM cell 420, etc.), and an output layer. Other neural network architectures are also supported.

During training, carefully calibrated noise (not shown for clarity) is added to the weights of autoencoder module 520 (i.e., embedder module 522 and recovery module 524), generator module 530 and discriminator module 540 to ensure each network upholds differential privacy, e.g., satisfies a privacy metric, to preserve patient privacy. To generate the synthetic data, weight noise generator 580 generates weight noise (Z) 583, which is received as input to generator module 530 and passed through recovery module 524 to postprocessor module 528 which outputs the final synthetic data $\hat{x}$. In many embodiments, weight noise (Z) 583 is a random vector of noise.

The embedded original data $x_e$ and the embedded synthetic data $\widehat{x_e}$ are used to train generator module 530 and discriminator module 540 rather than the original data x and the synthetic data $\hat{x}$. By reducing the dimensionality of the space in which generator module 530 and discriminator module 540 learn, these networks focus on and learn the most important parts or motifs of the traces.

Figure 6:
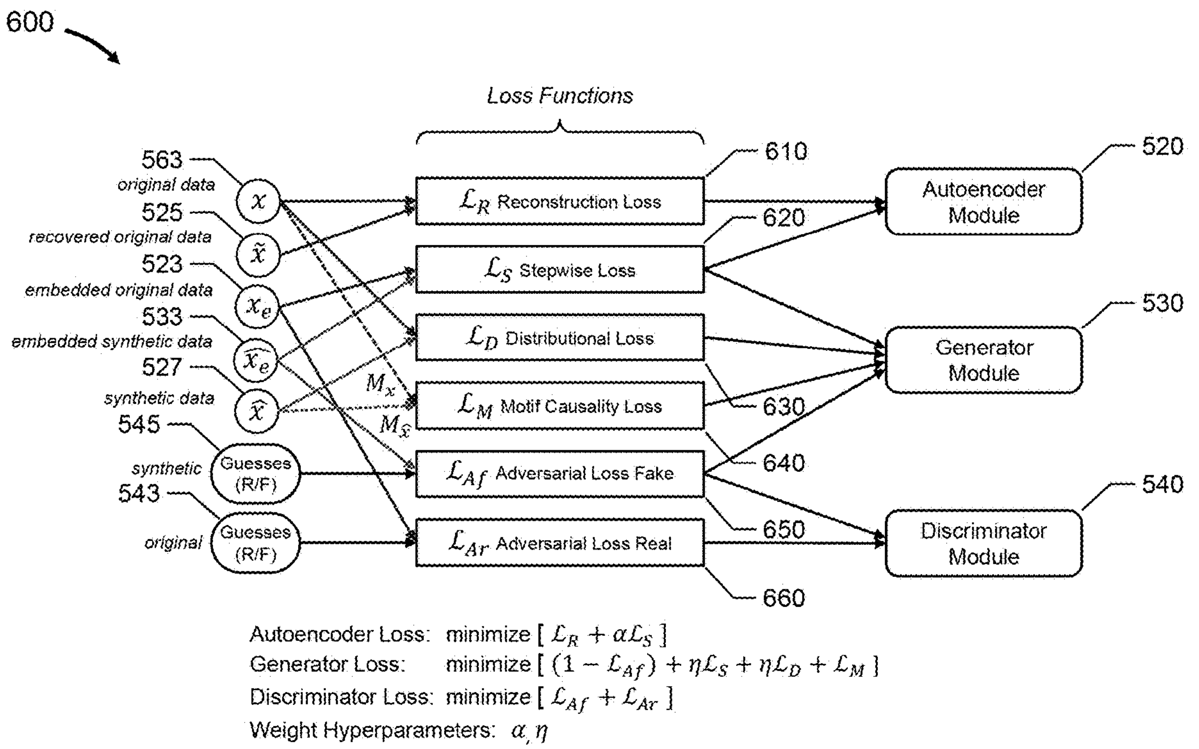
FIG. 6 depicts an example loss function diagram for training the DP-GAN depicted in FIG. 5, in accordance with embodiments of the present disclosure.

FIG. 6 depicts a loss function diagram 600 for training DP-GAN 500 depicted in FIG. 5, in accordance with embodiments of the present disclosure.

In many embodiments, the modules of DP-GAN 500 may be trained in a particular sequence. First, motif causality module 510 is trained, using original data $x_m$ (data 553), to generate aggregated motif causality matrix 513 ($M_A$). The remaining modules of DP-GAN 500 are then trained in sequence (e.g., within each epoch), using original data x (data 563) and aggregated motif causality matrix 513 ($M_A$), to generate synthetic data $\hat{x}$. In certain embodiments, autoencoder module 520 is trained, then generator module 530 and discriminator module 540 are adversarially trained, and then embedder module 522 of autoencoder module 520 is trained a second time.

In many embodiments, six loss functions are used to train autoencoder module 520, generator module 530 and discriminator module 540, including reconstruction loss ($L_R$) 610, stepwise loss ($L_S$) 620, distributional loss ($L_D$) 630, motif causality loss ($L_M$) 640, adversarial loss fake ($L_{Af}$) 650, and adversarial loss real ($L_{Ar}$) 660. Other loss functions, as well as subsets of these loss functions, are also supported.

Reconstruction loss ($L_R$) 610 is the root mean square error (RMSE) between original data x and recovered original data $\tilde{x}$. A "perfect" autoencoder perfectly reconstructs the original data, such that $x=\tilde{x}$.

Stepwise loss ($L_S$) 620 is the mean square error (MSE) between batches of embedded original data $x_e$ and batches of embedded synthetic data $\widehat{x_e}$. Generator module 530 compares, and learns to correct, the discrepancies between stepwise data distributions using stepwise loss ($L_S$) 620. In other words, generator module 530 learns to better generate the next time step batch of data by looking at the difference in its generated next step and the real next step.

Distributional loss ($L_D$) 630 is the moments loss between the distribution of original data x and the distribution of synthetic data $\hat{x}$. Generator module 530 learns to generate a diverse set of traces, and not the same type of trace over and over again, using distributional loss ($L_D$) 630.

Motif causality loss ($L_M$) 640 is the MSE between motif causality matrix computed on original data, $M_x$, and motif causality matrix computed on synthetic data, $M_{\hat{x}}$. Generator module 530 computes the motif causality matrix $M_{\hat{x}}$ after the set of embedded synthetic data $\widehat{x_e}$ is run back through recovery module 524 and postprocessor module 528 to generate the synthetic data in the original space $\hat{x}$. Generator module 530 learns to generate synthetic data that yields a realistic causal matrix (thereby identifying appropriate causal relationships from the motifs), and implicitly learns not to generate unrealistic motif sequences, using motif causality loss ($L_M$) 640.

Adversarial loss fake ($L_{Af}$) 650 is the binary cross entropy (BCE) between the discriminator guesses on the synthetic data $\hat{x}$, i.e., embedded synthetic guesses 545, and the ground truth, i.e., a vector of 1's.

Adversarial loss real ($L_{Ar}$) 660 is the BCE between the discriminator guesses on the original data x, i.e., embedded original guesses 543, and the ground truth, i.e., a vector of 0's.

Autoencoder module 520 is trained to minimize a weighted combination of reconstruction loss ($L_R$) 610 and stepwise loss ($L_S$) 620 ($\alpha$ is weight hyperparameter), as given by Equation 10, in order to avoid overspecialization.

$$\text{Minimize}[\mathcal{L}_R + \alpha\mathcal{L}_S] \qquad \text{Eq. 10}$$

Generator module 530 is trained to minimize a weighted combination of stepwise loss ($L_S$) 620, distributional loss ($L_D$) 630, motif causality loss ($L_M$) 640 and adversarial loss fake ($L_{Af}$) 650 (n is a weight hyperparameter), as given by Equation 11. Stepwise loss ($L_S$) 620 enables the dual training of autoencoder module 520 and generator module 530.

$$\text{Minimize}[(1 - \mathcal{L}_{AS}) + \eta\mathcal{L}_S + \eta\mathcal{L}_D + \mathcal{L}_M] \qquad \text{Eq. 11}$$

Discriminator module 540 is trained to minimize a weighted combination of adversarial loss fake ($L_{Af}$) 650 and adversarial loss real ($L_{Ar}$) 660, as given by Equation 12.

$$\text{Minimize}[\mathcal{L}_{Af} + \mathcal{L}_{Ar}] \qquad \text{Eq. 12}$$

In one embodiment, $\alpha$ is 0.1 and $\eta$ is 10; other values are also supported. These training objectives and loss functions train DP-GAN 500 to generate high quality, long time series synthetic data.

Figure 7:
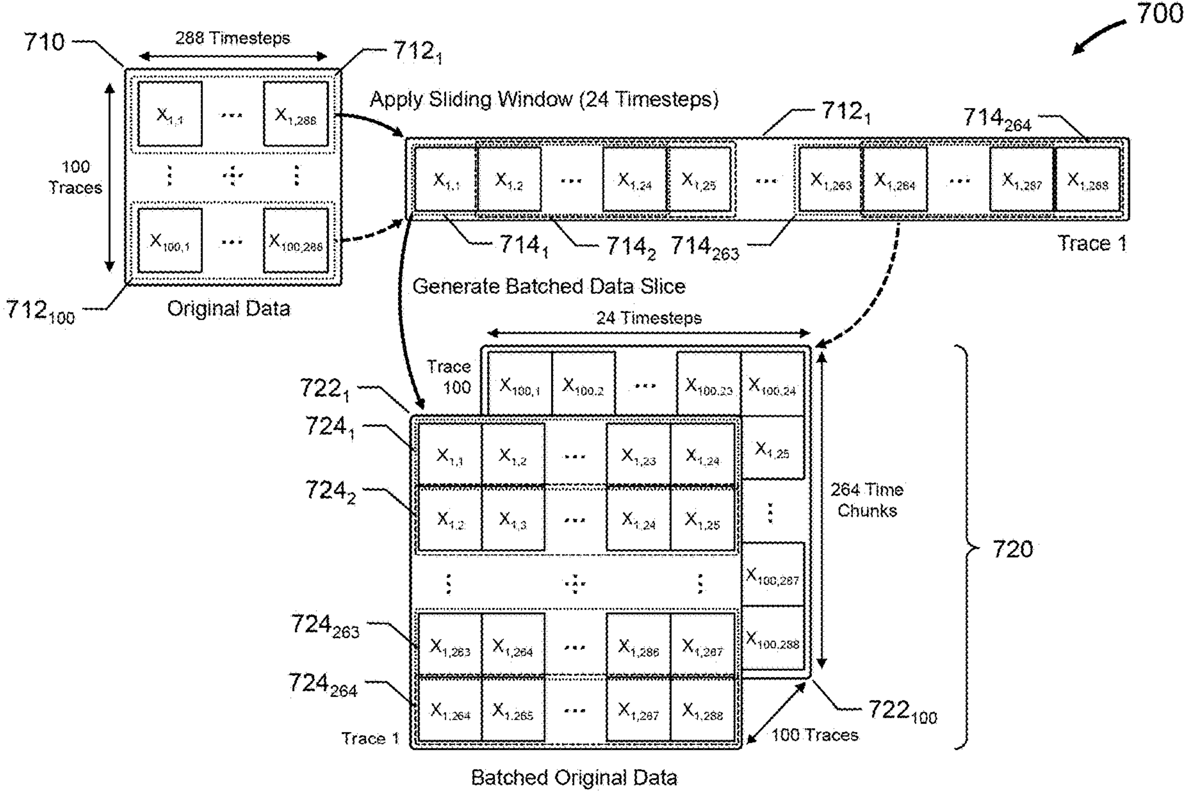
FIG. 7 depicts an example data flow diagram for generating batched original data for training the DP-GAN depicted in FIG. 5, in accordance with embodiments of the present disclosure.

FIG. 7 depicts data flow 700 for generating batched original data for training DP-GAN 500 depicted in FIG. 5, in accordance with embodiments of the present disclosure.

In the exemplary embodiment depicted in FIG. 7, original data 710 includes 100 traces, i.e., trace $\mathbf{712}_1, \ldots, \mathbf{712}_{100}$, and each trace includes 288 data values (time steps). For example, trace $\mathbf{712}_1$ includes original data $X_{1,1}, \ldots, X_{1,288}$, and so on; trace $712_{100}$ includes original data $X_{100,1}, \ldots, X_{100,288}$. In many embodiments, preprocessor module 526 preprocesses original data x (data 563) to generate batched original data x (as discussed above).

Preprocessor module 526 applies a sliding window (width 24, stride length 1) to each trace in original data 710 to expand each trace into a batched data slice including 264 time chunks, each time chunk including 24 data values (time steps). For trace $712_1$, the sliding window is applied to the first 24 data values, i.e., data value sequence 7141, to generate time chunk 7241 of batched data slice $722_1$, which includes $X_{1,1}, X_{1,2}, \ldots, X_{1,23}, X_{1,24}$. The sliding window is then moved one data value position to the right and applied to the next 24 data values, i.e., data value sequence $714_2$, to generate time chunk $724_2$ of batched data slice $722_1$, which includes $X_{1,2}, X_{1,3}, \ldots, X_{1,24}, X_{1,25}$. And so on. Data value sequence $714_{263}$ generates time chunk $724_{263}$ of batched data slice $722_1$, which includes $X_{1,263}, X_{1,264}, \ldots, X_{1,286}, X_{1,287}$, and data value sequence $714_{264}$ generates time chunk $724_{264}$ of batched data slice $722_1$, which includes $X_{1,264}, X_{1,265}, \ldots, X_{1,287}, X_{1,288}$. The remaining traces are processed in a similar manner; finally, trace $712_{100}$ generates batched data slice $722_{100}$. Batched original data 720 includes all of the batched data slices $722_i$, i.e., batched data slice $722_1, \ldots$, batched data slice $722_{100}$. Other methods for generating batched original data 720 are also supported.

Embedder module 522 then reduces the dimensionality of the batched original data x to generate an embedded set of traces, i.e., embedded original data $x_e$ (data 523). In the exemplary embodiment, embedder module 522 may reduce the number of chunks from 264 to 128 in each batched data slice to generate embedded original data $x_e$.

Figure 8A:
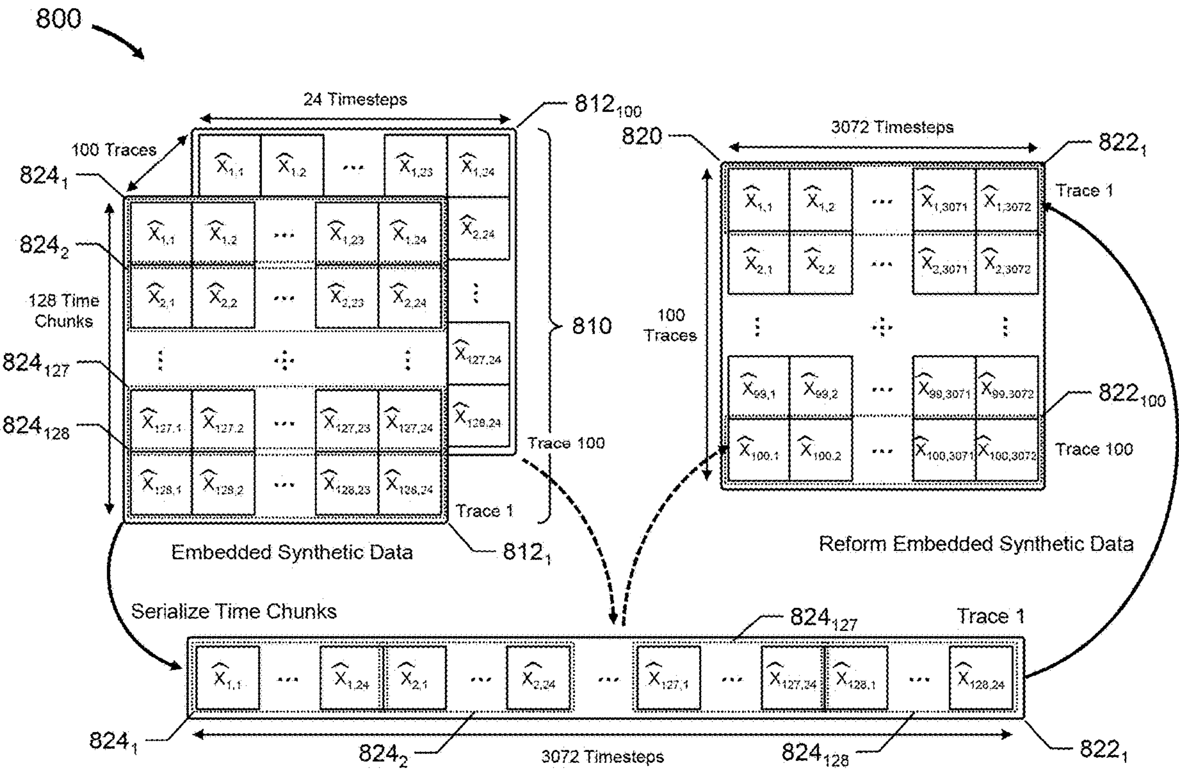
FIGS. 8A and 8B depict example data flow diagrams for generating synthetic data by the DP-GAN depicted in FIG. 5, in accordance with embodiments of the present disclosure.
Figure 8B:
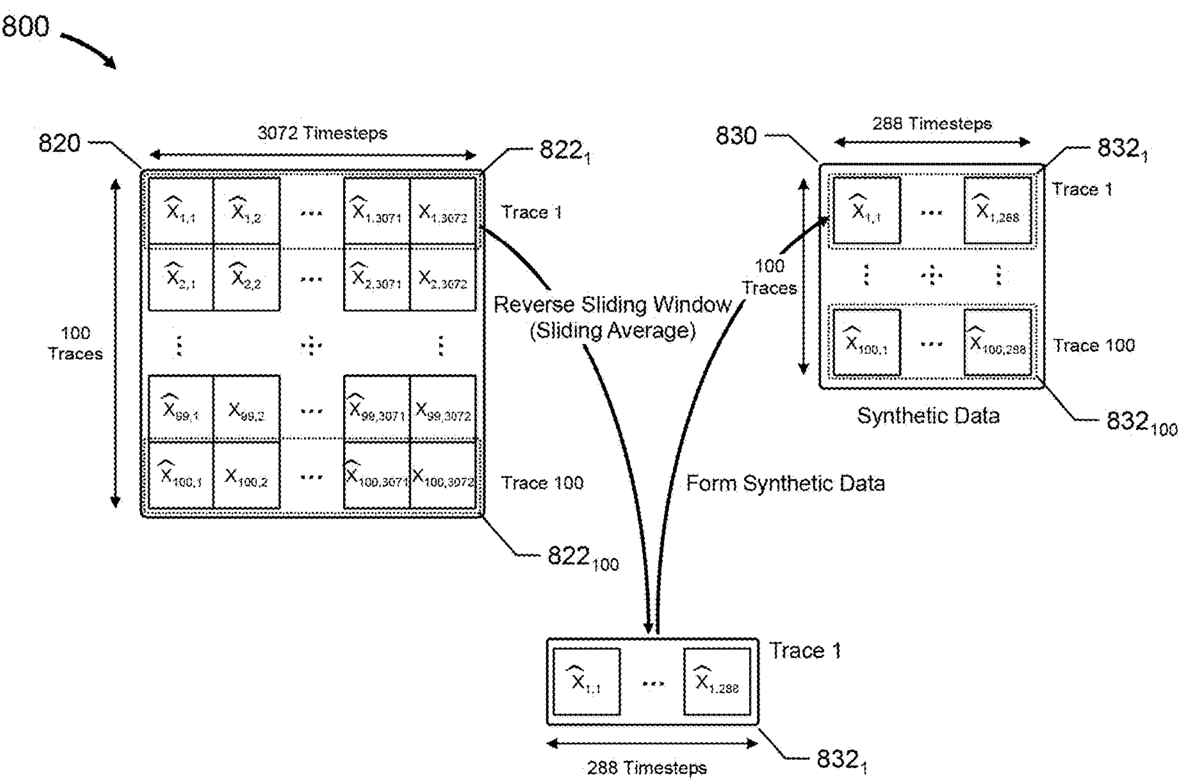

FIGS. 8A and 8B depict data flow 800 for generating synthetic data 830 by DP-GAN 500 depicted in FIG. 5, in accordance with embodiments of the present disclosure.

In many embodiments, postprocessor module 528 reconstructs the embedded synthetic data $\hat{x}_e$ (data 533) in the original data space to generate synthetic data $\hat{x}$ (data 573), which may be output as synthetic longitudinal time series data 570 (as discussed above).

In the exemplary embodiment depicted in FIGS. 8A and 8B, embedded synthetic data 810 includes 100 traces, i.e., trace $812_1, \ldots, 812_{100}$, each trace includes 128 time chunks, and each time chunk includes 24 data values (time steps). For example, trace $812_1$ includes time chunk $824_1, \ldots$, time chunk $824_{128}$; time chunk $824_1$ includes embedded synthetic data $X^h_{1,1}, \ldots, X^h_{1,24}, \ldots$, time chunk $824_{128}$ includes embedded synthetic data $X^h_{128,1}, \ldots, X^h_{128,24}$ ($X^h$ represents $\hat{X}$ in FIGS. 8A and 8B).

Postprocessor module 528 first serializes each trace $812_i$ of embedded synthetic data 810 into a single row of reformed embedded synthetic data 820. For example, trace $812_1$ is formed into serialized trace $822_1$ by first placing time chunk $824_1$ into the first row of reformed embedded synthetic data 820, placing time chunk 8242 into the first row of reformed embedded synthetic data 820 after time chunk $824_1$, and so on, until time chunk $824_{128}$ is placed into the first row of reformed embedded synthetic data 820 after time chunk 824127, thereby completing the formation of serialized trace $822_1$. The indexing for the elements of serialized trace $822_1$ is shown to transition from time chunk/time step-based indices (e.g., $X^h_{1,1}, \ldots, X^h_{1,24}, X^h_{128,1}, \ldots, X^h_{128,24}$, etc.) to trace/time step-based indices (e.g., $X^h_{1,1}, \ldots, X^h_{1,3072}, X^h_{100,1}, \ldots, X^h_{100,3072}$, etc.). The remaining traces $812_i$ of embedded synthetic data 810 are serialized in a similar manner, concluding with the formation of serialized trace $822_{100}$ from trace $812_{100}$.

Postprocessor module 528 then applies a reverse sliding window (i.e., a sliding average) to each serialized trace $822_i$ of reformed embedded synthetic data 820 to reconstruct the embedded synthetic data in the original space of 100 traces, each with 288 data values (time steps). Generally, the reverse sliding window averages groups of data values in each serialized trace $822_i$, based on the width (t time steps) and stride length (s time steps) of the window, to generate each synthetic trace $832_i$. For example, serialized trace $822_1$ is formed into synthetic trace $832_1$ by applying the reverse sliding window to data values $X^h_{1,1}, \ldots, X^h_{1,3072}$ to generate data values $X^h_{1,1}, \ldots, X^h_{1,288}$. And so on. Finally, serialized trace $822_{100}$ is formed into synthetic trace $832_{100}$ by applying the reverse sliding window to data values $X^h_{100,1}, \ldots, X^h_{100,3072}$ to generate data values $X^h_{100,1}, \ldots, X^h_{100,288}$. Synthetic data 830 includes synthetic trace $832_1, \ldots, 832_{100}$. Other methods for generating synthetic data 830 are also supported.

Figure 9A:
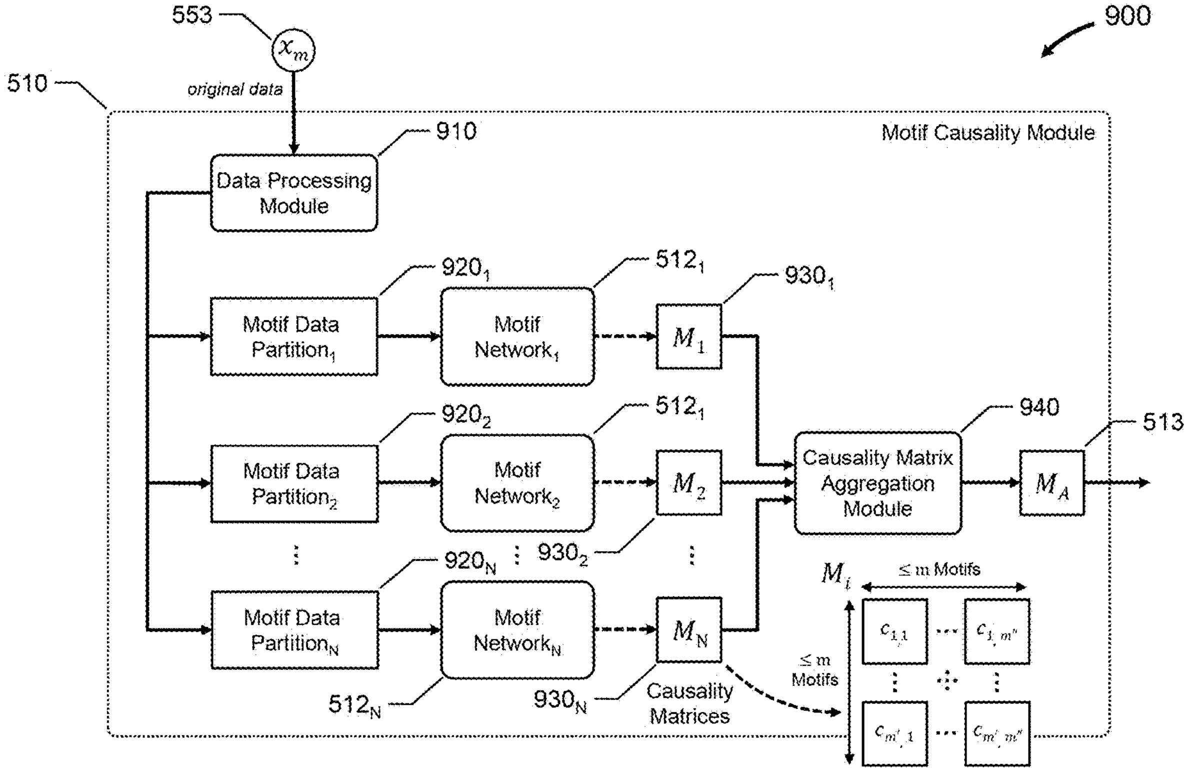
FIG. 9A depicts an example data flow diagram for a motif causality module, in accordance with embodiments of the present disclosure.

FIG. 9A depicts a data flow diagram 900 for motif causality module 510, in accordance with embodiments of the present disclosure.

Motif causality module 510 includes data processing module 910, a number (N) of motif networks $512_1, 512_2, \ldots, 512_N$, and motif causality matrix aggregation module 940. During the training of motif causality module 510, data processing module 910 generates a number (N) of non-overlapping motif data partitions $920_1, 920_2, \ldots, 920_N$ from original data $x_m$ (data 553). Each motif data partition $920_i$ includes data for different patients from original longitudinal time series data (set A) 550. Each motif network $512_1, 512_2, \ldots, 512_N$ receives a different motif data partition $920_i$, i.e., motif network $512_1$ receives motif data partition $920_1$, motif network $512_2$ receives motif data partition $920_2$, and so on.

Each motif network $512_i$ generates a motif causality matrix $930_i(M_i)$ based on the respective motif data partition $920_i$, i.e., motif network $512_1$ generates motif causality matrix $930_1$ ($M_1$) based on the motif data partition $920_1$, motif network $512_2$ generates motif causality matrix $930_2$ ($M_2$) based on the motif data partition $920_2$, and so on. As noted above, each motif causality matrix $930_i$ ($M_i$) expresses the relationships among motifs that motif network $512_i$ learns during training. Generally, motif causality matrix $930_i$ ($M_i$) includes motif causality values c and has a width≤m and a height≤m (where m is the number of motifs to be analyzed in the data partition, discussed below). Each causality factor $c_{j,k}$ expresses the strength of the relationship between two motifs (e.g., motif j and motif k), and may have values between 0 (i.e., indicating a weak relationship) and 1 (i.e., indicating a strong relationship). Other values are also supported.

Motif causality matrix aggregation module 940 aggregates motif causality matrices $930_1$ ($M_1$), $930_2$ ($M_2$), ..., $930_N$ (MN) into aggregated motif causality matrix 513 ($M_A$) to preserve patient privacy, i.e., to satisfy a privacy metric. Aggregated motif causality matrix 513 ($M_A$) is provided to generator module 530 during its training to focus generator module 530 on retaining the important motifs (events) within the traces of embedded original data $x_e$.

Figure 9B:
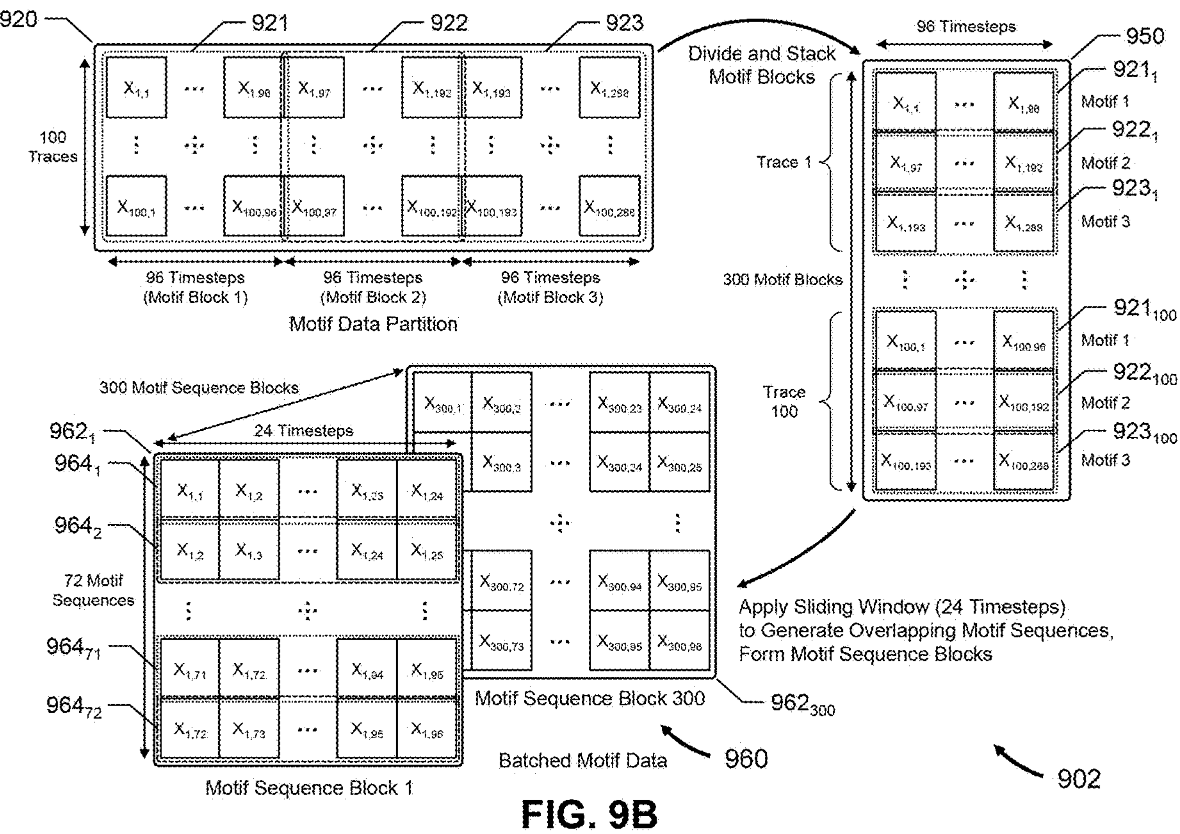
FIG. 9B depicts an example data flow diagram for generating motif sequence blocks for training the motif causality module depicted in FIG. 9A, in accordance with embodiments of the present disclosure.

FIG. 9B depicts data flow diagram 902 for generating batched motif data 960 for training motif causality module 510 depicted in FIG. 9A, in accordance with embodiments of the present disclosure.

After data processing module 910 generates each motif data partition $920_1, 920_2, \ldots, 920_N$, data processing module 910 further processes each motif data partition $920_1, 920_2, \ldots, 920_N$ to generate respective batched motif data 960.

In the exemplary embodiment depicted in FIG. 9B, motif data partition 920 includes 100 traces, and each trace includes 288 data values (time steps). For example, the first trace includes original data $X_{1,1}, \ldots, X_{1,288}$, and so on; the last trace includes original data $X_{100,1}, \ldots, X_{100,288}$. Other numbers of traces and numbers of data values (time steps) are also supported.

Motif data partition 920 may be notionally divided into a number of motif blocks, one motif block for each motif to be analyzed. Three motif blocks are depicted, and each motif block includes 96 data values (time steps) for each trace, i.e., motif block 921 for motif 1, motif block 922 for motif 2, and motif block 923 for motif 3. Motif block 921 includes data values $X_{1,1}, \ldots, X_{1,96}, \ldots, X_{100,1}, \ldots, X_{100,96}$. Motif block 922 includes data values $X_{1,97}, \ldots, X_{1,192}, \ldots, X_{100,97}, \ldots, X_{100,192}$. Motif block 923 includes data values $X_{1,193}, \ldots, X_{1,288}, \ldots, X_{100,193}, \ldots, X_{100,288}$. While motif data partition 920 may be divided into 2 motif blocks, motif data partition 920 is typically divided into 3 or more motif blocks.

Data processing module 910 divides motif blocks 921, 922 and 933 into separate motif blocks for each trace, and then stacks the separate motif blocks into motif block stack 950. For the first trace, motif block $\mathbf{921}_1$ includes data values $X_{1,1}, \ldots, X_{1,96}$, motif block $\mathbf{922}_1$ includes data values $X_{1,97}, \ldots, X_{1,192}$, and motif block $\mathbf{923}_1$ includes data values $X_{1,193}, \ldots, X_{1,288}$. And so on. For the last trace, motif block $\mathbf{921}_{100}$ includes data values $X_{100,1}, \ldots, X_{100,96}$, motif block $\mathbf{922}_{100}$ includes data values $X_{100,97}, \ldots, X_{100,192}$, and motif block $\mathbf{923}_{100}$ includes data values $X_{100,193}, \ldots, X_{100,288}$. Accordingly, motif block stack 950 includes 300 motif blocks.

Data processing module 910 then applies a sliding window (width 24, stride length 1) to each motif block in motif block stack 950 to expand each motif block into a motif sequence block that includes 72 overlapping motif sequences, each motif sequence including 24 data values (time steps).

For motif block $\mathbf{921}_1$, the sliding window is applied to the first 24 data values to generate motif sequence $\mathbf{964}_1$ of motif sequence block $\mathbf{962}_1$, which includes $X_{1,1}, X_{1,2}, \ldots, X_{1,23}, X_{1,24}$. The sliding window is then moved one data value position to the right and applied to the next 24 data values to generate motif sequence $\mathbf{964}_2$ of motif sequence block $\mathbf{962}_1$, which includes $X_{1,2}, X_{1,3}, \ldots, X_{1,24}, X_{1,25}$. And so on. For example, motif sequence $\mathbf{964}_{71}$ includes $X_{1,71}, X_{1,72}, \ldots, X_{1,94}, X_{1,95}$, and motif sequence $\mathbf{964}_{72}$ includes $X_{1,72}, X_{1,73}, \ldots, X_{1,95}, X_{1,96}$.

For motif block $\mathbf{922}_1$, the sliding window is applied to the data values $X_{1,97}, \ldots, X_{1,192}$ to generate motif sequence block $\mathbf{962}_2$ (not shown for clarity). For motif block $\mathbf{923}_1$, the sliding window is applied to the data values $X_{1,193}, \ldots, X_{1,288}$ to generate motif sequence block $\mathbf{962}_3$ (not shown for clarity). And so on for the remaining motif blocks. For example, for motif block $\mathbf{923}_{100}$, the sliding window is applied to the data values $X_{100,193}, \ldots, X_{100,288}$ to generate motif sequence block $\mathbf{962}_{300}$. Other methods for generating batched motif data 960 are also supported.

Figure 10A:
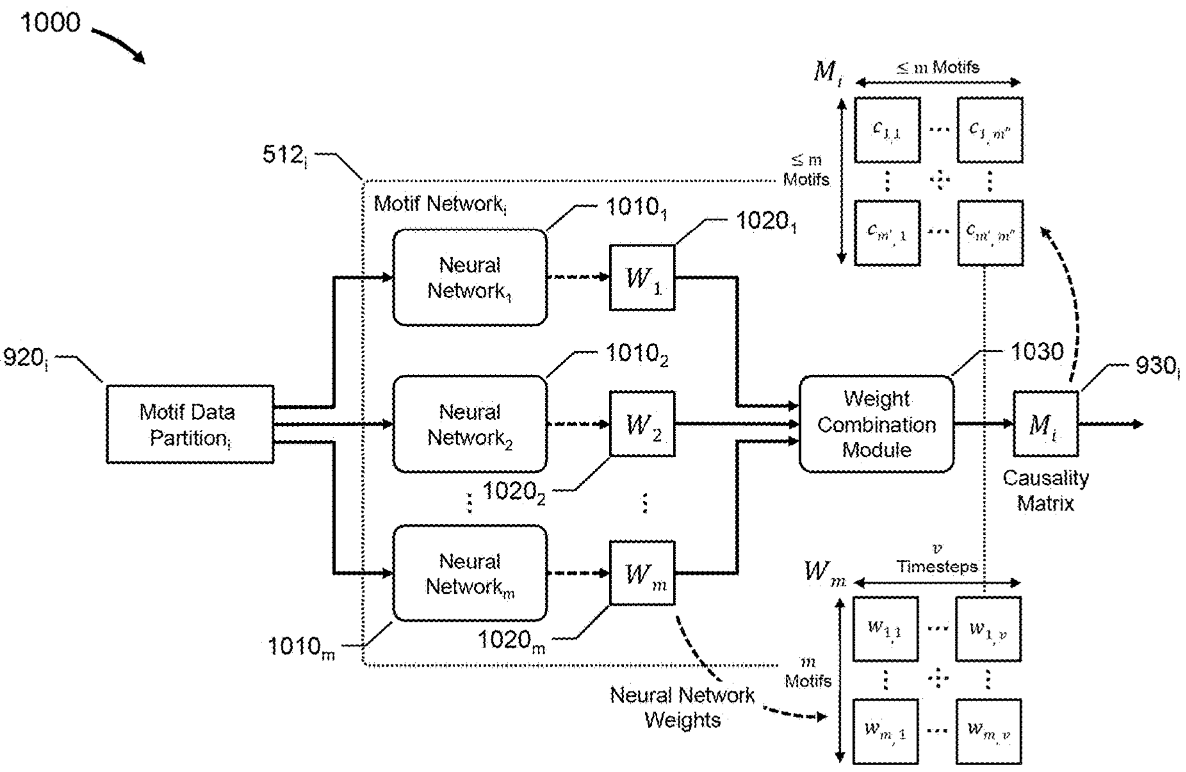
FIG. 10A depicts a data flow diagram for a motif network within the motif causality module depicted in FIG. 9A, in accordance with embodiments of the present disclosure.

FIG. 10A depicts a data flow diagram 1000 for motif network $\mathbf{512}_i$, in accordance with embodiments of the present disclosure.

Motif network $\mathbf{512}_i$ includes a number (m) of neural networks $\mathbf{1010}_1, \mathbf{1010}_2, \ldots, \mathbf{1010}_m$, and weight combination module 1030. The number m is the number of motifs that are being analyzed, as described above. Neural network $\mathbf{1010}_1$ includes weight matrix $\mathbf{1020}_1$ ($W_1$), neural network $\mathbf{1010}_2$ includes weight matrix $\mathbf{1020}_2$ ($W_2$), and so on. Neural network $\mathbf{1010}_m$ includes weight matrix $\mathbf{1020}_m$ ($W_m$).

Each neural network $\mathbf{1010}_j$ is trained using motif data partition $\mathbf{920}_i$, as discussed below. Weight combination module 1030 linearly combines weight matrices $\mathbf{1020}_1, \mathbf{1020}_2, \ldots, \mathbf{1020}_m$ to generate motif causality matrix $\mathbf{930}_i$. Generally, each weight matrix 1020; includes weights w and has a width equal to the sliding window width (e.g., 24 time steps) and a height equal to m.

Figure 10B:
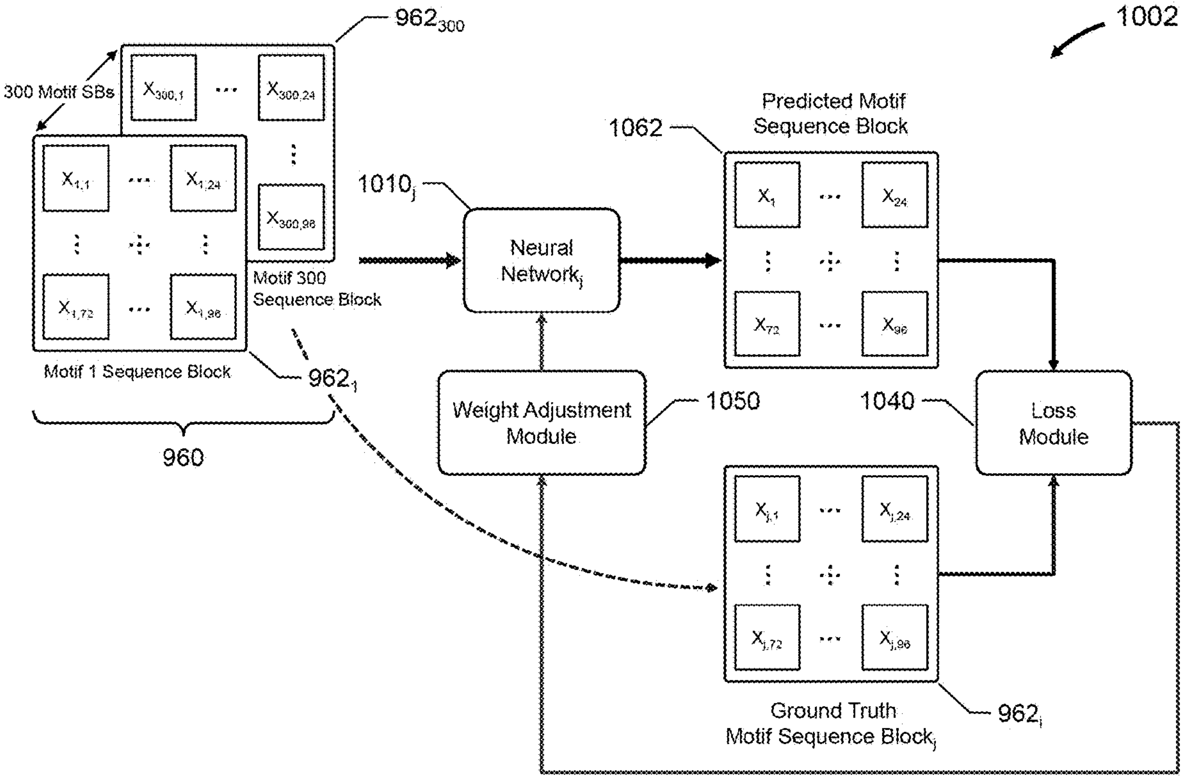
FIG. 10B depicts an example data flow diagram for training a neural network within the motif network depicted in FIG. 10A, in accordance with embodiments of the present disclosure.

FIG. 10B depicts data flow diagram 1002 for training neural network $\mathbf{1010}_j$ within motif network $\mathbf{512}_i$ depicted in FIG. 10A, in accordance with embodiments of the present disclosure.

In certain embodiments, loss module 1040 and weight adjustment module 1050 may be provided for each neural network $\mathbf{1010}_j$ within motif network $\mathbf{512}_i$. In other embodiments, loss module 1040 and weight adjustment module 1050 may be provided for motif network $\mathbf{512}_i$ and used to train each neural network $\mathbf{1010}_j$.

In many embodiments, neural network 1010; includes an input layer, at least one hidden layer, such as, for example, an RNN layer (e.g., hidden recurrent layer 320, hidden recurrent module 320', etc.) or LSTM layer (e.g., LSTM cell 420, etc.), and an output layer. In certain embodiments, a convolutional layer may precede the output layer. Other neural network architectures are also supported.

Generally, neural network $\mathbf{1010}_j$ is trained with respect to a particular "ground truth" motif sequence block $\mathbf{962}_j$ within batched motif data 960 to learn the causal relationships between ground truth motif sequence block $\mathbf{962}_j$ and all the other motif sequence blocks within batched motif data 960. More particularly, neural network $\mathbf{1010}_j$ generates a predicted motif sequence block 1062 based on batched motif data 960. Loss module 1040 determines whether the weights ($W_j$) for neural network $\mathbf{1010}_j$ should be adjusted by comparing predicted motif sequence block 1062 to ground truth motif sequence block $\mathbf{962}_j$ using a loss function, such as, for example, MSE, RMSE, etc.

Figure 11A:
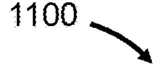
FIG. 11A depicts an example motif causality matrix, in accordance with embodiments of the present disclosure.
Figure 11A:
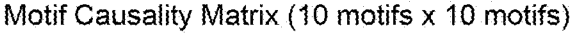
Figure 11A:
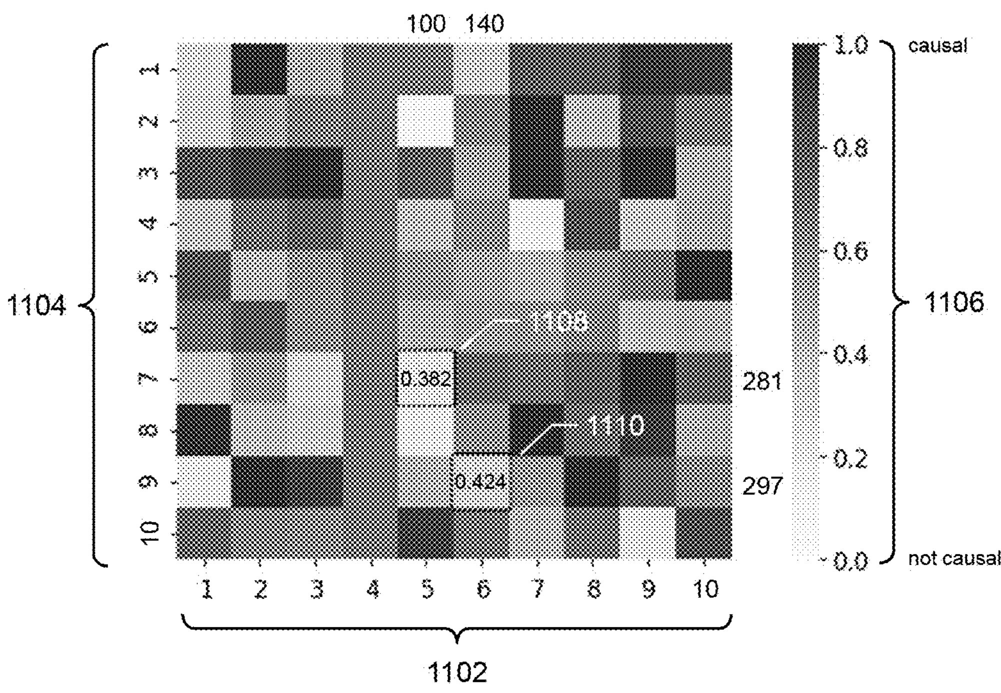

FIG. 11A depicts motif causality matrix 1100, in accordance with embodiments of the present disclosure.

Motif causality matrix 1100 is a 10×10 matrix which presents motif causality values for 100 pairs of motifs. X-axis 1102 includes 10 motif bins, Y-axis 1104 includes 10 motif bins, and scale 1106 ranges from 0 (i.e., no causal relationship between motifs) to 1 (strong causal relationship between motifs). For example, motif causality element 1120 has a value of 0.382 and indicates somewhat causal relationship between motif 100 (i.e., bin 5 on the X-axis) and motif 281 (i.e., bin 7 on the Y-axis). Motif causality element 1120 has a value of 0.424 and indicates a slightly higher causal relationship between motif 140 (i.e., bin 6 on the X-axis) and motif 297 (i.e., bin 9 on the Y-axis).

Figure 11B:
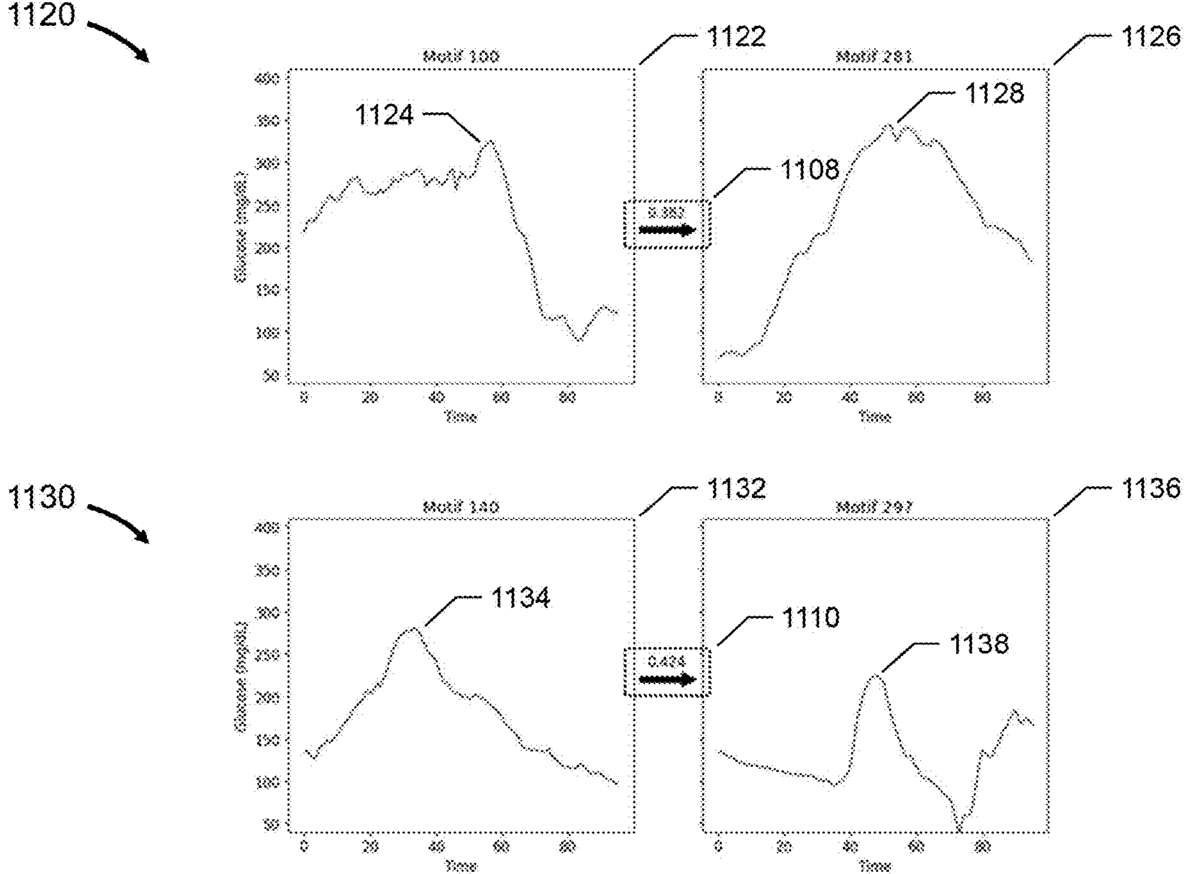
FIG. 11B depicts example motif time series data for two motif causality matrix entries, in accordance with embodiments of the present disclosure.

FIG. 11B depicts motif comparisons 1120 and 1130 for motif causality elements 1108 and 1110, respectively, in accordance with embodiments of the present disclosure.

Motif comparison 1120 includes graph 1122 depicting time series data 1124 (i.e., glucose values vs. time) for motif 100, graph 1126 depicting time series data 1128 (i.e., glucose values vs. time) for motif 281, and motif causality element 1108 having a value of value 0.382. Similarly, motif comparison 1130 includes graph 1132 depicting time series data 1134 (i.e., glucose values vs. time) for motif 140, graph 1136 depicting time series data 1138 (i.e., glucose values vs. time) for motif 297, and motif causality element 1110 having a value of value 0.424.

For medical longitudinal time series data, the sequence of important motifs is more informative than every single previous timestep. Traditional time series data generation methods, such as autoregressive models, assume that the time series is dependent on all previous time steps within the window, and generate a value for x at time t based on a sequence of the previous values of x. Importantly, these methods only conserve temporal relationships (e.g., information from previous time steps within the window), and ignore any other potentially informative relationships within the same time series (e.g., x) or between different time series.

Figures 12A, 12B:
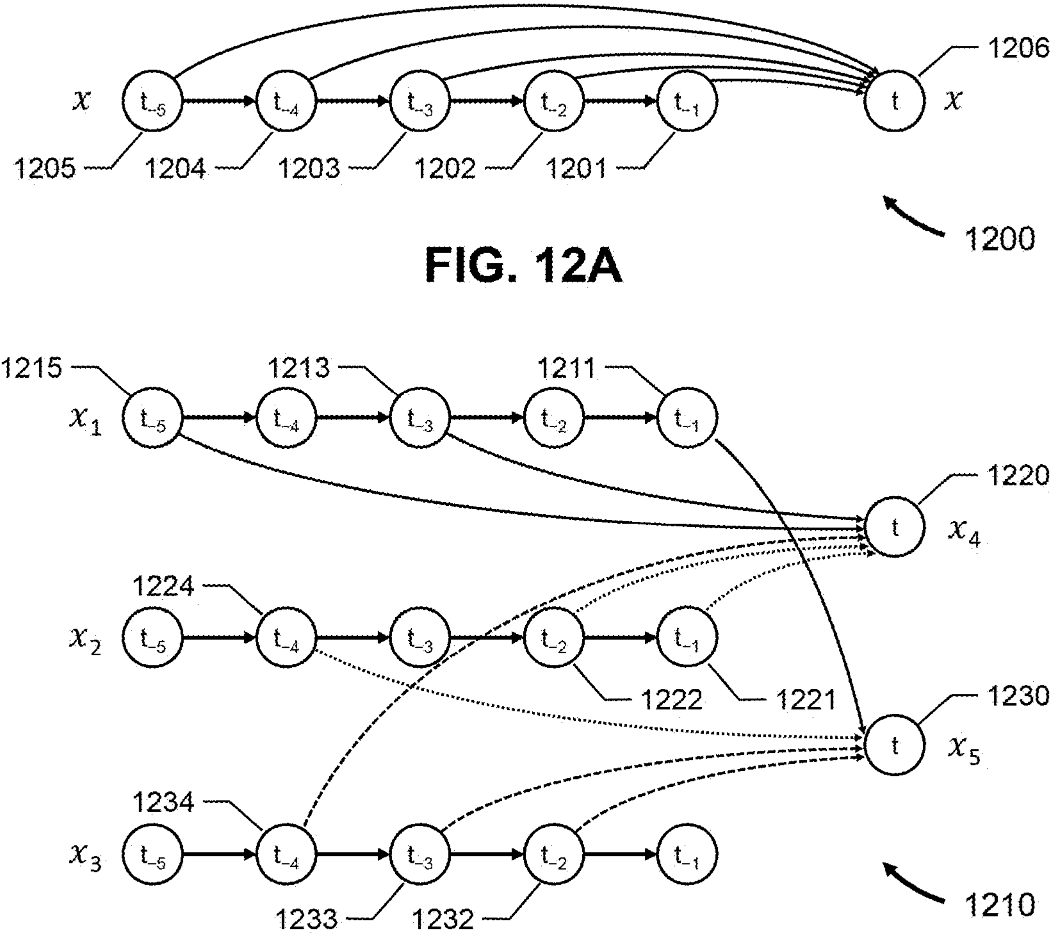
FIG. 12A depicts traditional time series data generation.
FIG. 12B depicts motif causality time series data generation, in accordance with embodiments of the present disclosure.

FIG. 12A depicts traditional time series data generation 1200.

The value of x at time step t (i.e., x value 1206) depends on the values of x at time steps t−1 (i.e., x value 1201), t−2 (i.e., x value 1202), t−3 (i.e., x value 1203), t−4 (i.e., x value 1204), and t−5 (i.e., x value 1205). While the previous values for x may be weighted in a linear combination, subject to dropout, etc., traditional methods heavily depend on window size and miss long term relationships between different time series.

FIG. 12B depicts motif causality time series data generation 1210, in accordance with embodiments of the present disclosure.

As shown in FIG. 12B, the value of $x_4$ at time step t (i.e., $x_4$ value 1220) depends on the values of $x_1$ at time t−3 (i.e., $x_1$ value 1213) and t−5 (i.e., $x_1$ value 1215), the values of $x_2$ at time t−1 (i.e., $x_2$ value 1221) and t−2 (i.e., $x_2$ value 1222), and the value of $x_3$ at time t−4 (i.e., $x_1$ value 1234). Similarly, the value of $x_5$ at time step t (i.e., $x_5$ value 1230) depends on the value of $x_1$ at time t−1 (i.e., $x_1$ value 1211), the value of $x_2$ at time t−4 (i.e., $x_2$ value 1224), and the values of $x_3$ at time t−2 (i.e., $x_3$ value 1232) and t−3 (i.e., $x_3$ value 1233).

Advantageously, motif causality time series data generation 1210 only uses the previous lags that have a causal impact, finds relationships across motifs from different time series and allows DP-GAN 500 to learn the relationships (patterns) amongst the sequences of important events in the traces that contribute to time series construction.

For long time series, this is particularly advantageous because networks can easily be overwhelmed when trained to learn from every previous time step. Instead, by only conserving relationships related to sequences of important motifs, DP-GAN 500 learns to output realistic sequences of time steps in the traces more quickly.

For example, for glucose traces, to predict the next glucose value at time t, a large peak in glucose (e.g., a hyperglycemic incident) 6 time steps or more in the past (e.g., earlier than t−6) is more informative than the immediate past 5 time steps (e.g., t−1, t−2, t−3, t−4, t−5). This is due to the strong effect of the event (e.g., we know that the glucose values must come back down from the peak, regardless of if the previous glucose values are 330→329 or 290→289). As a result, we can take advantage of the patterns amongst these types of events (for example, if we see a large peak motif, we know a decreasing slope motif will show up after it).

Figure 13:
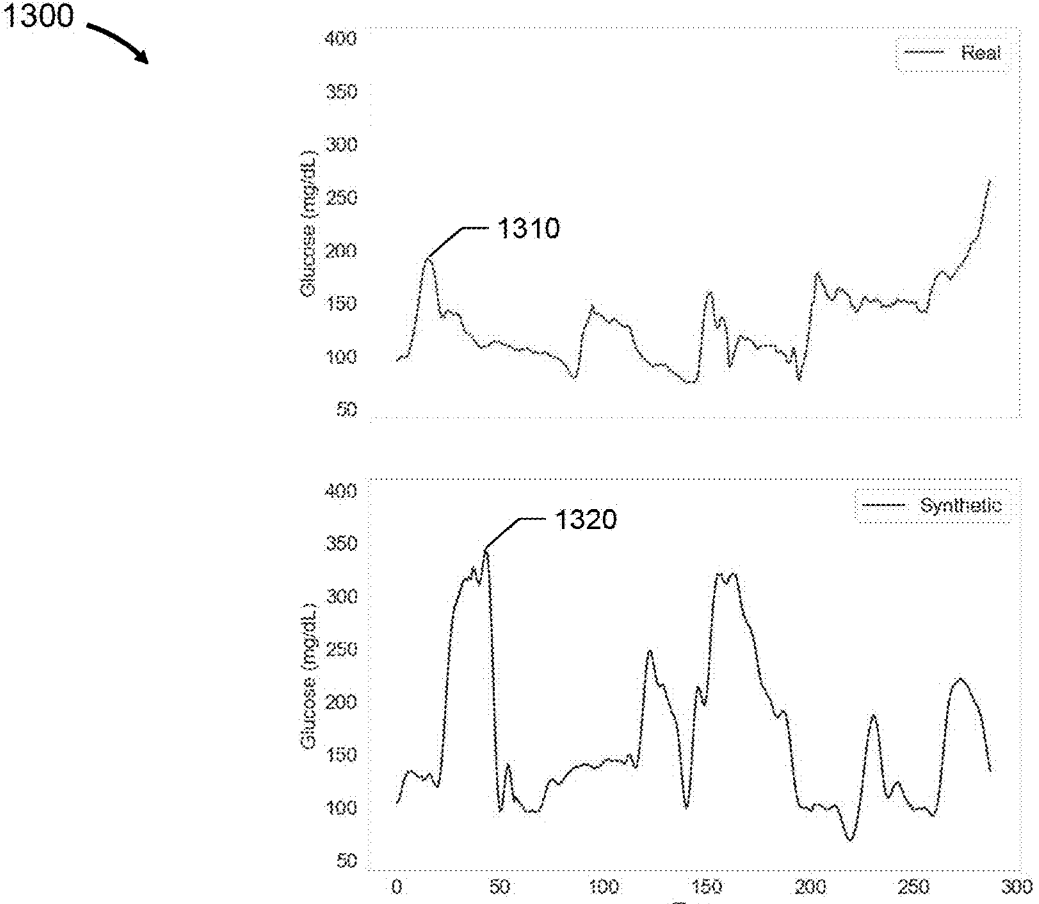
FIG. 13 depicts a comparison of longitudinal time series data and synthetic time series data, in accordance with embodiments of the present disclosure.

FIG. 13 depicts a comparison 1300 of longitudinal time series data and synthetic time series data, in accordance with embodiments of the present disclosure.

Longitudinal time series data 1310 includes measured glucose values (mg/dL) for 288 time steps. Synthetic time series data 1320 includes synthetic glucose values (mg/dL) for 288 time steps generated by DP-GAN 500. As we can see from the samples of the synthetic traces, patterns in the traces look very realistic (e.g., have very similar overall structures to the real traces in terms of sequences of peaks, troughs, etc.).

Figure 14:
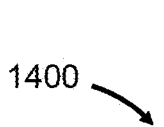
FIG. 14 depicts a flow chart representing functionality associated with generating synthetic data, in accordance with embodiments of the present disclosure.
Figure 14:
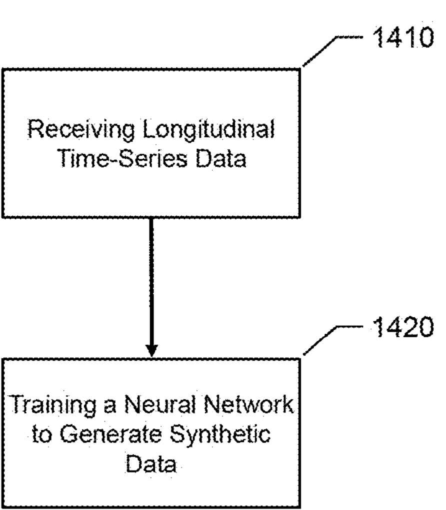

FIG. 14 depicts a flow chart 1400 representing functionality associated with generating synthetic data, in accordance with embodiments of the present disclosure.

At 1410, longitudinal time series data are received. In many embodiments, the longitudinal time series data are unlabeled and univariate.

As described above, the longitudinal time series data may be medical longitudinal time series data. Generally, a patient's medical longitudinal time series data are bounded and include at least 50 time steps. Certain medical longitudinal time series data may include 100 or more time steps, such as, for example, 288 time steps for 24 hours of continuous glucose monitoring (CGM) data (i.e., 12 measurements/hour).

At 1420, a neural network is trained, based on the longitudinal time series data, to generate synthetic time series data that satisfies a privacy metric.

In many embodiments, the neural network may be a DP-GAN, such as, for example, DP-GAN 500. Training DP-GAN 500 is described above with reference to FIGS. 6 to 11C. Additionally, as discussed above, aggregated motif causality matrix 513 ($M_A$) that preserves privacy is provided to generator module 530 during its training to focus generator module 530 on retaining the important motifs (events) within the traces of embedded original data $x_e$. Noise may also be added the weights of embedder module 522, recovery module 524, generator module 530 and discriminator module 540 to ensure each network upholds differential privacy.

The many features and advantages of the disclosure are apparent from the detailed specification, and, thus, it is intended by the appended claims to cover all such features and advantages of the disclosure which fall within the scope of the disclosure. Further, since numerous modifications and variations will readily occur to those skilled in the art, it is not desired to limit the disclosure to the exact construction and operation illustrated and described, and, accordingly, all suitable modifications and equivalents may be resorted to that fall within the scope of the disclosure.

What is claimed:

1. A method for generating synthetic data, the method comprising:

retrieving longitudinal time series data that are unlabeled and univariate;

training a motif causality module on a first subset of the longitudinal time series data for a first group of persons to generate an aggregate motif causality matrix, wherein the aggregate motif causality matrix includes motif causality values, each motif causality value expressing a strength of a relationship between two motifs, wherein the aggregate motif causality matrix identifies causal relationships between motifs within the first subset of the longitudinal time series data, wherein a motif is a short, ordered sequence of time steps from a time series that characterizes events in the longitudinal time series data;

training a neural network to generate synthetic time series data that satisfies a privacy metric based on the longitudinal time series data, wherein training the neural network includes conditioning a generator module on the aggregate motif causality matrix by supplying the aggregate motif causality matrix as an input to the generator module during the training when producing the synthetic time series data;

receiving, at an embedder module, a second subset of the longitudinal time series data for a second group of persons different than the first group of persons;

generating, by the embedder module, embedded time series data based on the second subset of the longitudinal time series data, the embedded time series data having a lower dimensionality than the second subset of the longitudinal time series data; and generating, by the generator module, embedded synthetic time series data based on the aggregate motif causality matrix and the embedded time series data.

2. The method of claim 1, wherein the longitudinal time series data include at least 50 measured glucose levels from each person of a plurality of persons.

3. The method of claim 1, wherein the privacy metric comprises a differential-privacy budget parameter that constrains a privacy loss for any single individual to a predefined threshold.

4. The method of claim 3, wherein the neural network is a differential-privacy generative adversarial network (DP-GAN).

5. The method of claim 4, wherein the motif causality module includes a plurality of motif networks, and the generating the aggregate motif causality matrix includes:

partitioning the first subset of the longitudinal time series data into data partitions, each data partition being associated with a different motif network and including a plurality of motifs, each motif being an ordered sequence of data values from the first subset of the longitudinal time series data;

for each motif network, generating a motif causality matrix from the associated data partition; and aggregating the motif causality matrices into the aggregate motif causality matrix based on the privacy metric.

6. The method of claim 5, wherein each motif network includes a plurality of recurrent neural networks (RNNs), each RNN receiving motif data from the associated data partition for a different motif.

7. The method of claim 4, wherein the training the neural network includes:

at a recovery module:

generating recovered longitudinal time series data based on the embedded time series data;

generating the synthetic time series data based on the embedded synthetic time series data, the synthetic time series data having a same dimensionality as the second subset of the longitudinal time series data;

at a discriminator module:

determining whether each data value in the embedded time series data is real or synthetic, and determining whether each data value in the embedded synthetic time series data is real or synthetic; and training, based on a plurality of loss functions, the embedder module, the recovery module, the generator module and the discriminator module to satisfy a performance metric and the privacy metric.

8. The method of claim 7, wherein the training the embedder module, the recovery module, the generator module and the discriminator module includes:

adding noise to weights associated with the embedder module, the recovery module, the generator module and the discriminator module based on the privacy metric.

9. The method of claim 8, wherein the training the embedder module, the recovery module, the generator module and the discriminator module includes:

training the embedder module and the recovery module based on a reconstruction loss and a stepwise loss;

training the generator module based on at least one of the stepwise loss, a distributional loss, a motif causality loss, and a synthetic data adversarial loss; and training the discriminator module based on the synthetic data adversarial loss and an embedded data adversarial loss.

10. The method of claim 9, wherein the motif causality loss is associated with data sequence patterns within the second subset of the longitudinal time series data.

11. The method of claim 7, wherein the embedder module, the recovery module, the generator module and the discriminator module each include an RNN.

12. A system for generating synthetic data, the system comprising:

a memory configured to store longitudinal time series data that are unlabeled and univariate; and at least one processor, coupled to the memory, configured to:

train a motif causality module on a first subset of the longitudinal time series data for a first group of persons to generate an aggregate motif causality matrix, wherein the aggregate motif causality matrix includes motif causality values, each motif causality value expressing a strength of a relationship between two motifs, wherein the aggregate motif causality matrix identifies causal relationships between motifs within the first subset of the longitudinal time series data, wherein a motif is a short, ordered sequence of time steps from a time series that characterizes events in the longitudinal time series data;

train a neural network to generate synthetic time series data that satisfies a privacy metric based on the longitudinal time series data, wherein to train the neural network includes conditioning a generator module on the aggregate motif causality matrix by supplying the aggregate motif causality matrix as an input to the generator module during the training when producing the synthetic time series data;

receive a second subset of the longitudinal time series data for a second group of persons different than the first group of persons;

generate embedded time series data based on the second subset of the longitudinal time series data, the embedded time series data having a lower dimensionality than the second subset of the longitudinal time series data; and generate embedded synthetic time series data based on the aggregate motif causality matrix and the embedded time series data.

13. The system of claim 12, wherein the privacy metric comprises a differential-privacy budget parameter that constrains a privacy loss for any single individual to a predefined threshold.

14. The system of claim 13, wherein:

the neural network is a differential-privacy generative adversarial network (DP-GAN) including the motif causality module having a plurality of motif networks, an embedder module, the generator module, a discriminator module and a recovery module;

the embedder module, the recovery module, the generator module and the discriminator module are trained based on the second subset of the longitudinal time series data, for a second group of persons different than the first group of persons.

15. The system of claim 14, wherein:

each motif network includes a plurality of recurrent neural networks (RNNs); and each RNN receives motif data for a different motif from an associated data partition of the first subset of the longitudinal time series data.

16. A non-transitory computer-readable medium storing instructions that, when executed by a processor, cause the processor to:

retrieve longitudinal time series data that are unlabeled and univariate;

train a motif causality module on a first subset of the longitudinal time series data for a first group of persons to generate an aggregate motif causality matrix, wherein the aggregate motif causality matrix includes motif causality values, each motif causality value expressing a strength of a relationship between two motifs, wherein the aggregate motif causality matrix identifies causal relationships between motifs within the first subset of the longitudinal time series data, wherein a motif is a short, ordered sequence of time steps from a time series that characterizes events in the longitudinal time series data;

train a neural network to generate synthetic time series data that satisfies a privacy metric based on the longitudinal time series data, wherein to train the neural network includes conditioning a generator module on the aggregate motif causality matrix by supplying the aggregate motif causality matrix as an input to the generator module during the training when producing the synthetic time series data;

receive a second subset of the longitudinal time series data for a second group of persons different than the first group of persons;

generate embedded time series data based on the second subset of the longitudinal time series data, the embedded time series data having a lower dimensionality than the second subset of the longitudinal time series data; and generate embedded synthetic time series data based on the aggregate motif causality matrix and the embedded time series data.

17. The non-transitory computer-readable medium of claim 16, wherein the privacy metric comprises a differential-privacy budget parameter that constrains a privacy loss for any single individual to a predefined threshold.

18. The non-transitory computer-readable medium of claim 17, wherein:

the neural network is a differential-privacy generative adversarial network (DP-GAN) including the motif causality module having a plurality of motif networks, an embedder module, the generator module, a discriminator module and a recovery module;

the embedder module, the recovery module, the generator module and the discriminator module are trained based on the second subset of the longitudinal time series data.

19. The non-transitory computer-readable medium of claim 18, wherein:

each motif network includes a plurality of recurrent neural networks (RNNs); and each RNN receives motif data for a different motif from an associated data partition of the first subset of the longitudinal time series data.

* * * * *